United States Patent
Nygaard et al.

(10) Patent No.: US 12,050,193 B2
(45) Date of Patent: Jul. 30, 2024

(54) MAGNESIUM ION SELECTIVE MEMBRANES

(71) Applicant: Radiometer Medical ApS, Bronshoj (DK)

(72) Inventors: Thomas Pedersen Nygaard, Bronshoj (DK); Palle Schneider, Bronshoj (DK); Peter Jakobsen Neilson, Bronshoj (DK); Thomas Steen Hansen, Bronshoj (DK); Thomas Laursen, Bronshoj (DK)

(73) Assignee: Radiometer Medical ApS, Brønshøj (DK)

( * ) Notice: Subject to any disclaimer, the term of this patent is extended or adjusted under 35 U.S.C. 154(b) by 801 days.

(21) Appl. No.: 17/256,282

(22) PCT Filed: Jun. 21, 2019

(86) PCT No.: PCT/EP2019/066503
§ 371 (c)(1),
(2) Date: Dec. 28, 2020

(87) PCT Pub. No.: WO2020/007623
PCT Pub. Date: Jan. 9, 2020

(65) Prior Publication Data
US 2021/0231601 A1   Jul. 29, 2021

(30) Foreign Application Priority Data

Jul. 4, 2018   (DK) .......................... PA 2018 00322

(51) Int. Cl.
| | | |
|---|---|---|
| G01N 27/333 | (2006.01) | |
| B01D 67/00 | (2006.01) | |
| B01D 71/30 | (2006.01) | |
| G01N 33/50 | (2006.01) | |

(52) U.S. Cl.
CPC ..... *G01N 27/3335* (2013.01); *B01D 67/0002* (2013.01); *B01D 71/301* (2022.08); *G01N 33/50* (2013.01)

(58) Field of Classification Search
None
See application file for complete search history.

(56) References Cited

FOREIGN PATENT DOCUMENTS

| | | |
|---|---|---|
| JP | 2002-510540 A | 4/2002 |
| JP | 56-92422 A | 2/2015 |
| WO | WO 92/16831 | 10/1992 |

OTHER PUBLICATIONS

P. Buhlmann, et al., "Carrier-Based Ion-Selective Electrodes and Bulk Opotodes. 2. Ionophores for Potentiometric and Optical Sensors", Chemical Reviews, 98(4): p. 1593-1688, June (Year: 1998).*
Adhikari, Basudam et al., "Polymers in sensor applications," Prog. Polym. Sci., 29, pp. 699-766 (2004).
Meyerhoff, Mark E. et al., "Ion-Selective Electrodes," Anal. Chem., 54, pp. 27R-44R (1982).
Thomas, J. D. R. , "Solvent Polymeric Membrane Ion-Selective Electrodes," Analytica Chimica Acta,, vol. 180, pp. 289-297 (1986).
International Search Report for International Application No. PCT/EP2019/066503, Sep. 26, 2019 (three pages).
Written Opinion of the International Searching Authority for International Application No. PCT/EP2019/066503 (nine pages).
Goldberg, H.D. et al., "Ion-Selective Sensors Incorporating Strongly Adhesive Polymeric Membranes," IEEE 4th Technical Digest, pp. 169-172 (1990).
Müller, Martin et al., "Magnesium Selective Electrode for Blood Serum Studies and Water Harness Measurement," Microchim, ACTA [wien], III, pp. 283-290 (1988).
Office Action—Japanese Patent App. No. 2021-500127—issued Mar. 29, 2022.

* cited by examiner

*Primary Examiner* — J. Christopher Ball
(74) *Attorney, Agent, or Firm* — FINNEGAN, HENDERSON, FARABOW, GARRETT & DUNNER, LLP

(57) ABSTRACT

Magnesium ion selective electrode membranes and the preparation thereof. The membranes are rendered highly selective for magnesium ions by the addition of acidic groups to the preferably PVC membrane, either by introducing a lipophilic compound comprising an acidic group covalently linked to a C4-C18 alkyl-substituted phenyl group (e.g. bis-4-octylphenyl phosphoric acid) into the membrane comprising the magnesium selective ionophore (e.g. a neutral ionophore 1,10-phenanthroline derivative) or by covalently linking an acidic (e.g. a carboxylic) group to the ionophore (e.g. a 1,10-phenanthroline derivative).

22 Claims, 2 Drawing Sheets

MAGNESIUM ION SELECTIVE MEMBRANES

This application is a national stage filing under 35 U.S.C. § 371 of International Application No. PCT/EP2019/066503, filed on Jun. 21, 2019, which claims priority of Danish Patent Application No. PA 2018 00322, filed on Jul. 4, 2018. The contents of these applications are each incorporated herein by reference in their entirety.

FIELD OF THE INVENTION

The invention relates to magnesium ion selective membranes and the preparation thereof, to electrodes and potentiometric sensors comprising such membranes and the use thereof for determining the magnesium ion concentration in samples.

BACKGROUND OF THE INVENTION

Magnesium is a common metal in the human body and plays an important role in chemical and biochemical processes. Magnesium in the body is either protein-bound, complexed to anions or present as a free ionized fraction (iMg). The iMg fraction plays several physiological roles, e.g. as an ion channel adjuster in nerve conduction or skeletal, cardiac or uterine muscle contraction. A high prevalence of hypomagnesemia (11%) and hypermagnesemia (9.3%) has been found in a study amongst hospitalized patients (Wong et al. (1983) Am J Clin Pathol 79:348).

Specific measurement of iMg is challenging and, historically, clinical laboratories have often relied on total magnesium assays. Magnesium ion selective sensors have been described in WO92/16831 (Nova Biomedical Corp.), which discloses a magnesium selective membrane including a 1,10-phenanthroline as a magnesium ion selective compound. WO2015/160755 (Siemens Healthcare Diagnostics Inc.) describes a membrane for detecting ionized magnesium comprising ionophores having a tripodal stereochemical structure, a lipophilic borate salt and a polymer matrix.

However, rendering membranes highly selective for iMg remains a challenge, in particular in obtaining selectivity for magnesium ions over other cations, such as calcium ions. In addition to having limited selectivity, magnesium ion selective membranes described in the art are often suboptimal in terms of stability, interference, drift and rapid start-up time. Adjustments to improve membranes on one of these parameters sometimes affect other parameters negatively.

Thus, there is a need for improved magnesium ion sensors that are highly selective for magnesium, yet remain stable, resistant to interference and drift, and have a rapid start-up time. These needs are addressed by the current invention.

SUMMARY OF THE INVENTION

In a first aspect, the invention provides a magnesium ion selective membrane comprising:
a. an ionophore; and
b. a lipophilic compound comprising an acidic group, wherein the lipophilic compound is a compound of the Formula I:

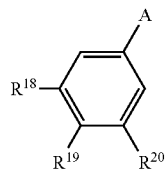

wherein A comprises an acidic group,
wherein one, two or all three of $R^{18}$, $R^{19}$ and $R^{20}$ is a $C_{4-18}$ group, which is a $C_{4-18}$alkyl group, a $C_{4-18}$alkenyl group, a $C_{4-18}$alkynyl group, or an amide-containing $C_{4-18}$ group,
wherein said $C_{4-18}$ group is linear at positions 1, 2 and 3, counting from the phenyl group, or in total only has one side chain at said positions 1, 2 and 3,
and wherein the others of $R^{18}$, $R^{19}$ and $R^{20}$ independently are hydrogen, or a linear $C_{1-18}$ alkyl group,
or a salt of said lipophilic compound.

In a further aspect, the invention provides a magnesium ion selective membrane comprising
i) an ionophore covalently linked to an acidic group via a spacer wherein said spacer comprises at least one carbon atom or
ii) a salt thereof, i.e. a salt of said ionophore covalently linked to an acidic group via a spacer.

In a further aspect, the invention relates to a process for preparing a magnesium ion selective membrane of the invention by mixing the components in a solvent, dispensing the resulting solution on a desired support and allowing the solvent to evaporate.

In a further aspect, the invention provides an electrode for determining the magnesium ion concentration of a liquid sample comprising the membrane of the invention as defined herein.

In an even further aspect, the invention provides a potentiometric sensor for determining the magnesium ion concentration of a liquid sample comprising a membrane of the invention or an electrode of the invention.

Furthermore, the invention relates to a method for determining the magnesium ion concentration of a liquid sample comprising contacting said sample with an electrode according to the invention or a potentiometric sensor according to the invention and determining the magnesium ion concentration based on signal provided by said electrode or potentiometric sensor. The invention also relates to a method for diagnosing a disease or disorder comprising performing the method for determining the magnesium ion concentration according to the invention on a sample of a subject.

These and other aspects and embodiments of the invention are described in further detail below.

DETAILED DESCRIPTION OF THE INVENTION

Definitions

Figure 1:
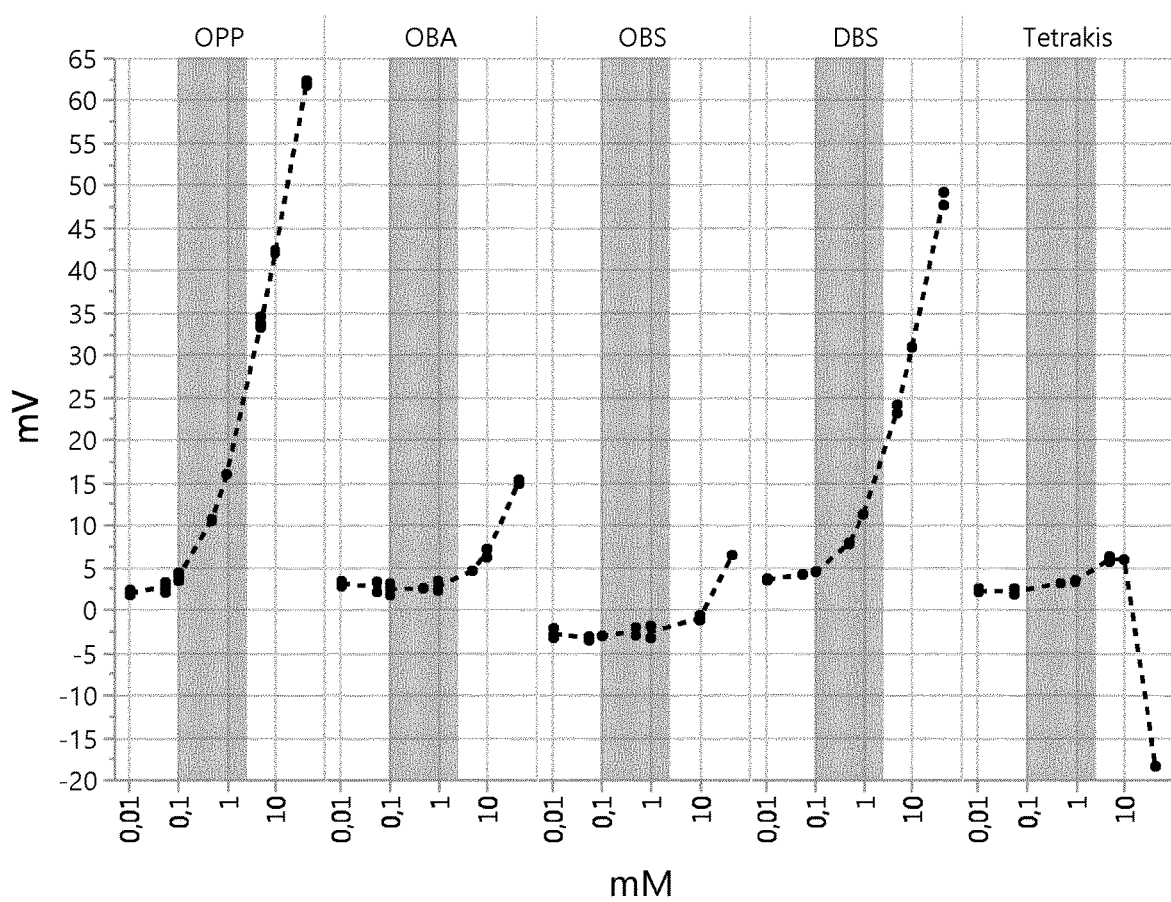
FIG. 1. Signals in mV as function of true cMg values as recorded for the FIM-solutions used to determine the selectivity constants ($KMgc_a$) and sensitivities (S) of ion selective electrodes prepared with membrane IDs: "OPP", "OBA", "OBS", "DBS" and "Tetrakis". Gray shaded areas indicate the physiological relevant measurement range (0.1-2.5 mM) for ionized magnesium. The x-axis is logarithmic.

The term "selective" when used herein in the context of a membrane refers to a preference for a particular ion. "selective" when used herein does not mean absolute or exclusive selectivity, i.e. a membrane can be selective for multiple ions, e.g. magnesium ions as well as calcium ions.

When used herein, the term "ionophore" refers to a compound that reversibly binds ions, e.g. a compound that can transport ions across a membrane.

The term "lipophilic" when used herein, in particular in the context of a "lipophilic compound", refers to the ability of a chemical compound to dissolve in fats, oils, lipids, or non-polar solvents.

The term "acidic group" refers to a group capable of ionizing to donate a hydrogen ion to a base.

The term "salt" when used herein refers to a deprotonated form of an acid together with a cationic species to counterbalance the negative charge thereof.

When used herein, the term "substituted form" of 1,10-phenanthroline refers to a substance which comprises a 1,10-phenanthroline skeleton containing one or more substitutions thereto. The term "substitution" refers to the replacement of a hydrogen on 1,10-phenanthroline with a group R or residue R. Similarly, "substituted aryl" refers to an aryl group wherein a hydrogen has been replaced with a different residue or group.

The term "$C_{XX-YY}$" in the context of a chemical group indicates that the group contains from XX to YY carbon atoms, i.e. any number starting from XX up to and including YY, for example a $C_{1-18}$ alkyl group contains 1, 2, 3, 4, 5, 6, 7, 8, 9, 10, 11, 12, 13, 14, 15, 16, 17 or 18 carbon atoms. Unless specified otherwise, such a group may be linear or branched.

When referring to chemical groups, the terms "alkyl", "aryl", "alkenyl" and "alkynyl" have their usual meaning in the art. In some embodiments, such groups comprise no more than 18 carbon atoms. The term "branched alkyl" refers to an alkyl group which is not fully linear, i.e. has at least one side-chain.

The term "concentration" when used herein in the context of determining a concentration of ions, such as magnesium ions, in a sample, refers to the stoichiometric concentration of the ion in a standardized solution matrix (reference scale) having an ion activity which is equal to that of the measured sample, cf. IFCC guidelines (Ben Rayana et al. (2008) Clin Chem Lab Med 46(1):21)

When used herein in connection with a polymer, the term molecular weight refers to the weight average molecular weight, calculated by:

$M_w = \Sigma W_i M_i$, wherein $W_i$ is the weight fraction of polymer with molecular weight $M_i$

Further Aspects and Embodiments of the Invention

The inventors have developed magnesium ion selective membranes that have improved selectivity for magnesium ions compared to membranes previously described in the art. In addition, the membranes of the invention are stable, resistant to interference and drift and have a rapid start-up time.

The improvement in selectivity is achieved by the addition of acidic groups to the membrane, either by introducing a lipophilic compound comprising an acidic group into the membrane or by covalently linking an acidic group to the ionophore used in the membrane.

Without being bound by any specific theory, it is hypothesized that structures such as the ones depicted below may be formed, favoring interaction of the ionophore with a magnesium ion rather than e.g. a larger calcium ion.

Structure A

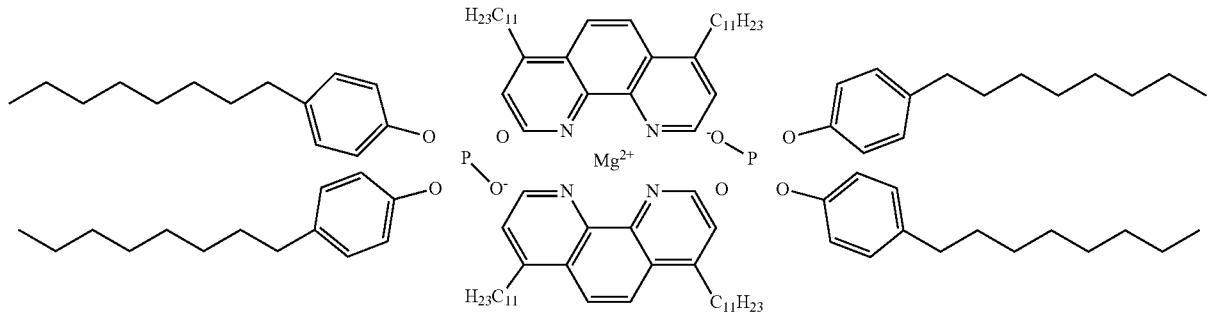

Structure B

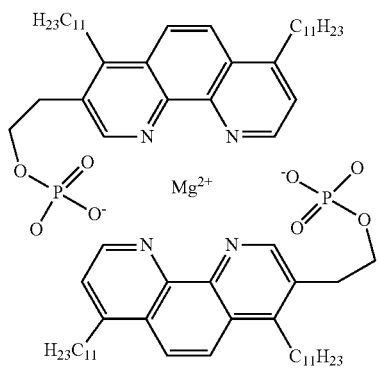

Accordingly, as described above, in a first aspect, the invention relates to a magnesium ion selective membrane comprising:
a. an ionophore; and
b. a lipophilic compound comprising an acidic group, wherein the lipophilic compound is a compound of the Formula I:

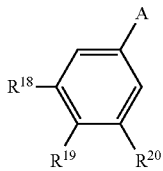

wherein A comprises an acidic group,
wherein one, two or all three of $R^{18}$, $R^{19}$ and $R^{20}$ is a $C_{4-18}$ group, which is a $C_{4-18}$alkyl group, a $C_{4-18}$alkenyl group, a $C_{4-18}$alkynyl group, or an amide-containing $C_{4-18}$ group,
wherein said $C_{4-18}$ group is linear at positions 1, 2 and 3, counting from the phenyl group, or in total only has one side chain at said positions 1, 2 and 3,
and wherein the others of $R^{18}$, $R^{19}$ and $R^{20}$ independently are hydrogen, or a linear $C_{1-18}$ alkyl group
or a salt of said lipophilic compound.

For the avoidance of doubt, the phrase "or in total only has one side chain at said positions 1, 2, and 3" herein means that each $C_{4-18}$ group in total only has one side-chain at said positions 1, 2, 3. Thus, in embodiments where two or more of $R^{18}$, $R^{19}$ and $R^{20}$ are $C_{4-18}$ groups, two or more of these $C_{4-18}$ groups may have one side-chain at position 1, 2 or 3.

For illustration, the following formula shows an embodiment wherein $R^{18}$ and $R^{20}$ are hydrogen and $R^{19}$ is a linear $C_8$ alkyl group without side chain. Positions 1, 2 and 3 are indicated:

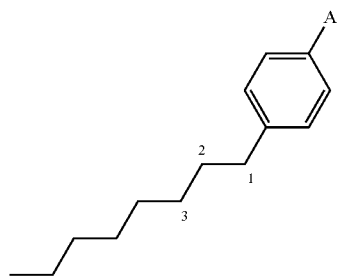

Furthermore, as mentioned above, in a further aspect, the invention provides a magnesium ion selective membrane comprising
i) an ionophore covalently linked to an acidic group via a spacer wherein said spacer comprises at least one carbon atom or
ii) a salt thereof, i.e. a salt of said ionophore covalently linked to an acidic group via a spacer.

Ionophores

The magnesium ion selective membrane of the invention comprises an ionophore or a mixture of ionophores. Ionophores used in the membrane of the invention may be charged or not charged (neutral). In some embodiments, the ionophore is lipophilic.

In a preferred embodiment, the ionophore is a phenanthroline compound which is 1,10-phenanthroline or a substituted form thereof. Such compounds have e.g. been described in WO92/16831 (Nova Biomedical Corp.). 1,10-phenanthroline has the following structure:

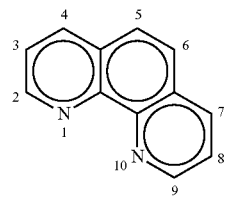

In one embodiment, the carbon atoms at positions 2 and 9 of the phenanthroline compound are bonded to a hydrogen.

In one embodiment, the ionophore is a compound of the Formula II:

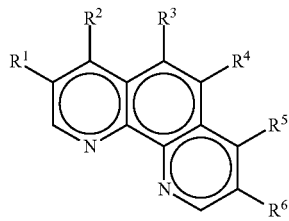

wherein each of $R^1$-$R^6$ is any of:
H;
any of F, Cl, Br, I, $NO_2$, CN, or $CF_3$;
$C_{1-18}$ alkyl;
$C_{1-18}$ aryl;
$C_{1-18}$ alkenyl;
$(CH_2)_m Y$, wherein m is 0 or an integer from 1 to 4, Y is any of $-OR^7$, $-NR^7R^8$, $-OCOR^7$, $-NR^7COR^B$, $-COR^7$, $-COOR^7$, $-SO_3R^7$, $-OSiR^7R^8R^9$, $-PO_4R^7R$, $-PO_3R^7R^8$, wherein each of $R^7$, $R^8$, and $R^9$ are any of H, alkyl, branched alkyl, aryl, or substituted aryl; or $C_n-R^{10}R^{11}$, wherein n is 0 or an integer between 1 and 17 inclusive, $R^{10}$ is C, N, NCO, or $CH_2-Z-CH_2$ wherein Z is any of O, NH, S, OCO, or CO, $R^{11}$ is a compound of the Formula III:

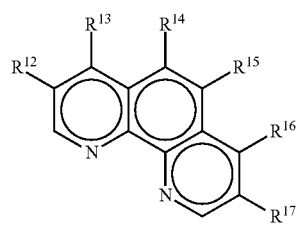

and $R^{11}$ is linked to $R^{10}$ at any of positions 3, 4, 5, 6, 7, or 8 of $R^{11}$, $R^{12}$-$R^{17}$ are any of H, $C_{1-18}$ alkyl, $C_{1-18}$ aryl, or deleted, provided that if $R^{11}$ is linked to $R^{10}$ at position 3 of $R^{11}$ then $R^{12}$ is deleted, if $R^{11}$ is linked to $R^{10}$ at position 4 of $R^{11}$ then $R^{13}$ is deleted, if $R^{11}$ is linked to $R^{10}$ at position 5 of $R^{11}$ then $R^{14}$ is deleted, if $R^{11}$ is linked to $R^{10}$ at position 6 of $R^{11}$ then $R^{15}$ is deleted, if $R^{11}$ is linked to $R^{10}$ at position 7 of $R^{11}$ then $R^{16}$ is deleted, if $R^{11}$ is linked to $R^{10}$ at position 8 of $R^{11}$ then $R^{17}$ is deleted, provided that one of $R^1$-$R^6$ is other than H and that each of the C atoms at positions 2 and 9 of the 1,10-phenanthroline is bonded, by the bond which does not participate in the fused ring structure, to an H.

In a further embodiment, $R^1$ to $R^6$ include a total of at least 6 carbon atoms, e.g. 6, 7, 8, 9 10 or 11 carbon atoms, such as a total of at least 11 carbon atoms, e.g. between 11 and 18 carbon atoms.

In another embodiment, one or more of $R^1$, $R^2$, $R^3$, $R^4$, $R^5$ and $R^6$ is an alkyl or aryl group having between 1 and 18 carbon atoms. For example, one or two groups selected from $R^1$, $R^2$, $R^3$, $R^4$, $R^5$ and $R^6$ may be an alkyl or aryl group having between 1 and 18 carbon atoms and the others are hydrogen, e.g. $R^1$ and $R^2$, $R^1$ and $R^3$, $R^1$ and $R^4$, $R^1$ and $R^5$, $R^1$ and $R^6$, $R^2$ and $R^3$, $R^2$ and $R^4$, $R^2$ and $R^5$, $R^2$ and $R^6$, $R^3$ and $R^4$, $R^3$ and $R^5$, $R^3$ and $R^6$, $R^4$ and $R^5$, $R^4$ and $R^6$ or $R^5$ and $R^6$ are alkyl or aryl groups having between 1 and 18 carbon atoms and the other groups are hydrogen.

In another embodiment, one or more of $R^1$, $R^2$, $R^3$, $R^4$, $R^5$ and $R^6$ is an alkyl group having between 1 and 18 carbon atoms. For example, one or two groups selected from $R^1$, $R^2$, $R^3$, $R^4$, $R^5$ and $R^6$ may be an alkyl group having between 1 and 18 carbon atoms and the others are hydrogen, e.g. $R^1$ and $R^2$, $R^1$ and $R^3$, $R^1$ and $R^4$, $R^1$ and $R^5$, $R^1$ and $R^6$, $R^2$ and $R^3$, $R^2$ and $R^4$, $R^2$ and $R^5$, $R^2$ and $R^6$, $R^3$ and $R^4$, $R^3$ and $R^5$, $R^3$ and $R^6$, $R^4$ and $R^5$, $R^4$ and $R^6$ or $R^5$ and $R^6$ are alkyl groups having between 1 and 18 carbon atoms and the other R groups are hydrogen.

In another embodiment, one or more of $R^1$, $R^2$, $R^3$, $R^4$, $R^5$ and $R^6$ is an alkyl group having between 6 and 18 carbon atoms. For example, one or two groups selected from $R^1$, $R^2$, $R^3$, $R^4$, $R^5$ and $R^6$ may be an alkyl group having between 6 and 18 carbon atoms and the others are hydrogen, e.g. $R^1$ and $R^2$, $R^1$ and $R^3$, $R^1$ and $R^4$, $R^1$ and $R^5$, $R^1$ and $R^6$, $R^2$ and $R^3$, $R^2$ and $R^4$, $R^2$ and $R^5$, $R^2$ and $R^6$, $R^3$ and $R^4$, $R^3$ and $R^5$, $R^3$ and $R^6$, $R^4$ and $R^5$, $R^4$ and $R^6$ or $R^5$ and $R^6$ are alkyl groups having between 6 and 18 carbon atoms and the others are hydrogen.

In another embodiment, only one of $R^1$, $R^2$, $R^3$, $R^4$, $R^5$ and $R^6$ is an alkyl group having between 1 and 18 carbon atoms, such as between 6 and 18 carbon atoms, e.g. between 11 and 18 carbon atoms and the other R groups are hydrogen.

In another embodiment, $R^2$ and/or $R^5$ is an alkyl group having between 1 and 18 carbon atoms, such as between 6 and 18 carbon atoms, e.g. between 11 and 18 carbon atoms and the other R groups are hydrogen. In another embodiment, $R^2$ and/or $R^5$ is an aryl group having between 1 and 18 carbon atoms.

In a preferred embodiment, the ionophore is 4-undecyl-1,10-phenanthroline or 4,7-diundecyl-1,10-phenanthroline.

Substituted 1,10-phenanthroline compounds may be synthesized by standard techniques known to those skilled in the art. For example, the synthesis of 4- and 4,7-substituted 1,10-phenanthrolines are described in Lund et al., J. Chem. Eng. Data, 26: 227-29 (1981), hereby incorporated by reference. Methyl groups can provide a handle for the attachment of the desired side-chain in the synthesis of other 1,10-phenanthroline derivatives, and methyl substituted 1,10-phenanthrolines are commercially available. For example, 4-methyl, 5-methyl, 6-methyl, 7-methyl, 3,6-dimethyl, 5,7-dimethyl, 4,7-dimethyl, and 5,6-dimethyl-1,10-phenanthroline are all available from Aldrich Chemical Co. 4-undecyl-1,10-phenanthroline and 4,7-diundecyl-1,10-phenanthroline may e.g. be synthesized as described in WO92/16831 (Nova Biomedical Corp.).

In another embodiment, the magnesium ion selective membrane comprises an ionophore having a tripodal stereochemical structure, e.g. a tripodal structure such as the ones described in WO2015/160755 (Siemens Healthcare Diagnostics Inc.).

Thus, in one embodiment, the ionophore is a compound according to Formula IV (also termed ETH5506 in the art):

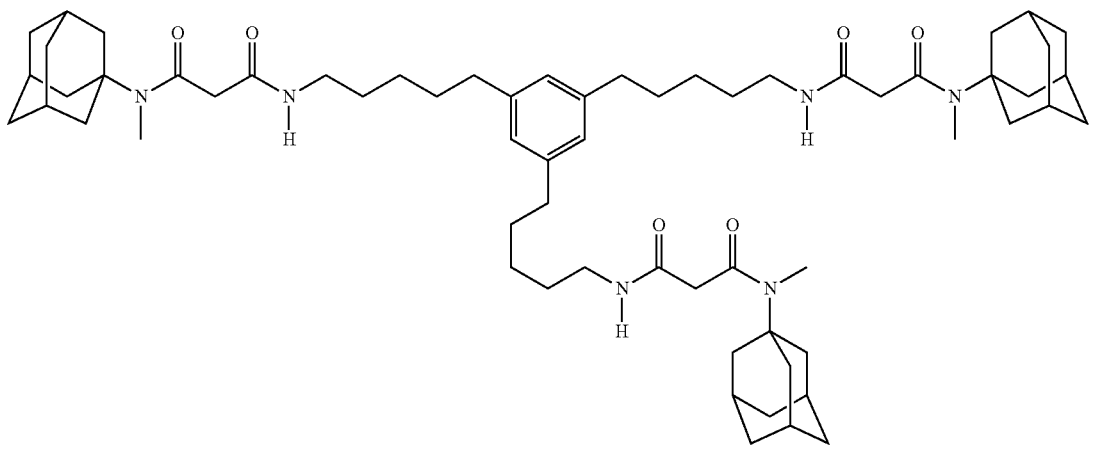 [SMILES: CN(C(=O)CC(=O)NCCCCCc1cc(CCCCCNC(=O)CC(=O)N(C)C23CC4CC(CC(C4)C2)C3)cc(CCCCCNC(=O)CC(=O)N(C)C23CC4CC(CC(C4)C2)C3)c1)C12CC3CC(CC(C3)C1)C2]

In another embodiment, the ionophore is a compound according to Formula V (also termed ETH5504 in the art):

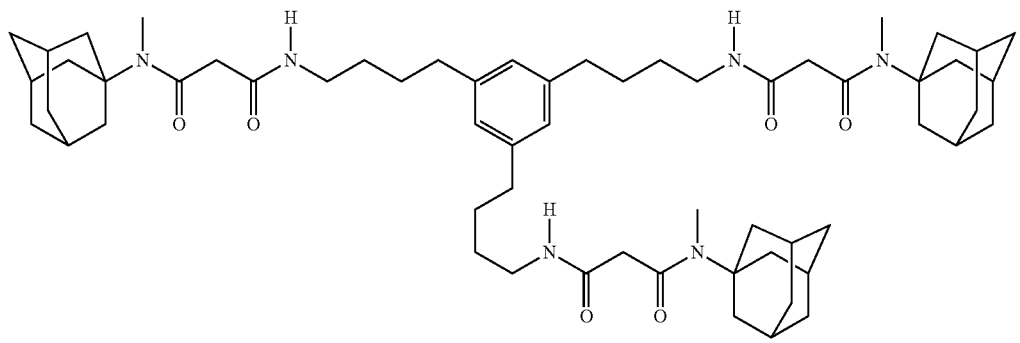 [SMILES: CN(C(=O)CC(=O)NCCCCc1cc(CCCCNC(=O)CC(=O)N(C)C23CC4CC(CC(C4)C2)C3)cc(CCCCNC(=O)CC(=O)N(C)C23CC4CC(CC(C4)C2)C3)c1)C12CC3CC(CC(C3)C1)C2]

In another embodiment, the ionophore is a compound according to Formula VI (also termed ETH3832 in the art):

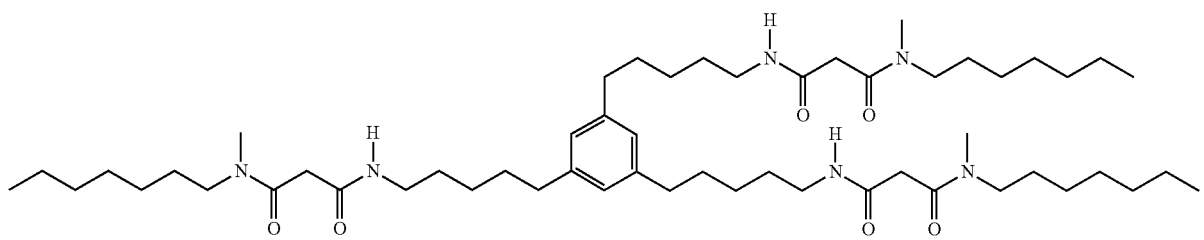 [SMILES: CCCCCCCN(C)C(=O)CC(=O)NCCCCCc1cc(CCCCCNC(=O)CC(=O)N(C)CCCCCCC)cc(CCCCCNC(=O)CC(=O)N(C)CCCCCCC)c1]

In another embodiment, the ionophore is a compound according to Formula VII, wherein n is an integer from 6 to 8 (termed ETH5282 in the art when n is 6; termed ETH7025 in the art when n is 8):

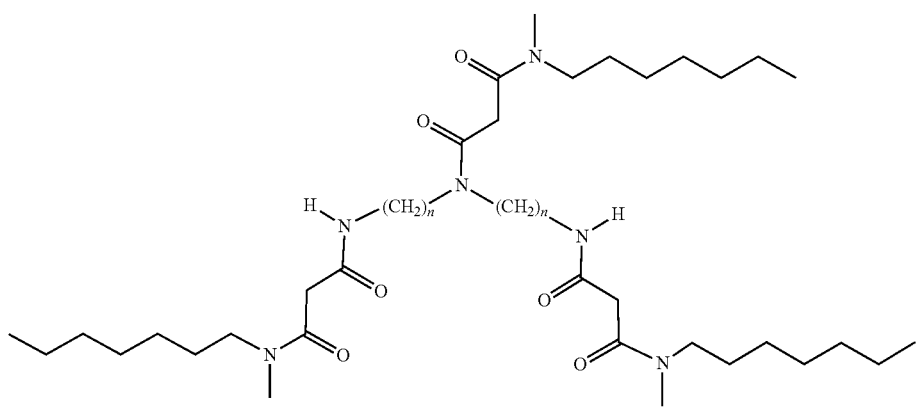

In another embodiment, the ionophore is one of the ionophores described in Table 8 of IUPAC 2000 Part I Inorganic cations Pure Appl Chem 72:1851, e.g. $Mg^{2+}$-1, $Mg^{2+}$-2 $Mg^{2+}$-3, $Mg^{2+}$-4, $Mg^{2+}$-5, $Mg^{2+}$-6, $Mg^{2+}$-7, $Mg^{2+}$-8, $Mg^{2+}$-9, $Mg^{2+}$-10, $Mg^{2+}$-11, $Mg^{2+}$-12, $Mg^{2+}$-13, $Mg^{2+}$-14, $Mg^{2+}$-15, $Mg^{2+}$-16, $Mg^{2+}$-17, $Mg^{2+}$-18, $Mg^{2+}$-19, $Mg^{2+}$-20, $Mg^{2+}$-21, $Mg^{2+}$-22, $Mg^{2+}$-23, $Mg^{2+}$-24, $Mg^{2+}$-25, $Mg^{2+}$-26, $Mg^{2+}$-27, $Mg^{2+}$-28, $Mg^{2+}$-29, $Mg^{2+}$-30, $Mg^{2+}$-31, $Mg^{2+}$-32, $Mg^{2+}$-33, $Mg^{2+}$-34, $Mg^{2+}$-35, $Mg^{2+}$-36, $Mg^{2+}$-37, $Mg^{2+}$-38, $Mg^{2+}$-39, $Mg^{2+}$-40, $Mg^{2+}$-41, $Mg^{2+}$-42, $Mg^{2+}$-43, $Mg^{2+}$-44, $Mg^{2+}$-45, $Mg^{2+}$-46, $Mg^{2+}$-47, $Mg^{2+}$-48, $Mg^{2+}$-49, $Mg^{2+}$-50, $Mg^{2+}$-51, $Mg^{2+}$-52, $Mg^{2+}$-53, $Mg^{2+}$-54, $Mg^{2+}$-55 or $Mg^{2+}$-56.

In another embodiment, the ionophore is one of the ionophores described in Bühlmann et al. (1998) Chem. Rev. 98:1593, e.g. $Mg^{2+}$-1, $Mg^{2+}$-2 $Mg^{2+}$-3, $Mg^{2+}$-4, $Mg^{2+}$-5, $Mg^{2+}$-6, $Mg^{2+}$-7, $Mg^{2+}$-8, $Mg^{2+}$-9, $Mg^{2+}$-10, $Mg^{2+}$-11, $Mg^{2+}$-12, $Mg^{2+}$-13, $Mg^{2+}$-14, $Mg^{2+}$-15 or $Mg^{2+}$-16.

In another embodiment, the ionophore is ETH 5220 (Zhang et al. (2011) Am. J. Biomed. Sci. 3:301) or ETH 2001, ETH 2002, ETH 2003 or ETH 2022 (Zhang et al. (2000) Anal. Sci. 16:11).

In another embodiment, the ionophore is ETH 1001, DBM, ETH 1117, cyclo(LPro-DLeu)$_s$, ETH 1224, ETH 2220, ETH 4030, ETH 5214, ETH 5282 or ETH 7025, all described in Spichiger (1993) Electroanalysis 5: 739.

In another embodiment, the ionophore is one of the ionophores described in Suzuki et al. (1995) Anal. Chem. 67:324 (herein incorporated by reference), preferably K22B5, an 18-membered diaza-crown having two malonamide side chains with an adamantyl group, or a variant thereof, such as K22B1B5 (Siswanta et al. (1997) Anal. Sci. 13:429.

In a preferred embodiment, the ionophore is 1,2-bis (diarylphosphine oxide)benzene (Saleh (1994) J. Electroanalytical Chem. 373:89) or methyl phenyl semicarbazone (Chandra et al. (2013) J. Chem., http://dx.doi.org/10.1155/2013/189464).

Lipophilic Compounds

As mentioned, in a first aspect, the invention provides a magnesium ion selective membrane comprising:
a. an ionophore; and
b. a lipophilic compound comprising an acidic group, wherein the lipophilic compound is a compound of the formula I:

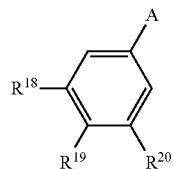

wherein A comprises an acidic group,
wherein one, two or all three of $R^{18}$, $R^{19}$ and $R^{20}$ is a $C_{4-18}$ group, which is a $C_{4-18}$alkyl group, a $C_{4-18}$alkenyl group, a $C_{4-18}$alkynyl group, or an amide-containing $C_{4-18}$ group, wherein said $C_{4-18}$ group is linear at positions 1, 2 and 3, counting from the phenyl group, or in total only has one side chain at said positions 1, 2 and 3, and
wherein the others of $R^{18}$, $R^{19}$ and $R^{20}$ independently are hydrogen, or a linear $C_{1-18}$ alkyl group, or
a salt of said lipophilic compound.

Accordingly, the membrane of this aspect of the invention comprises a lipophilic compound according to formula I or a salt thereof.

In one embodiment, the acidic group comprised within group A of formula I is a carboxylic acid, a sulfonic acid, a sulfuric acid monoester, a sulfonamide, a phosphonic acid, a phosphoric acid, an arsenic acid, a sulfinic acid or a thiocarboxylic acid.

In one embodiment, the acidic group comprised within group A of formula I is a carboxylic acid. For example, group A may be a carboxylic acid group according to formula IX, a carbonic acid group according to formula X, an oxalic acid monoester group according to formula XI or a dicarboxylic acid monoester group according to formula XII:

Formula IX
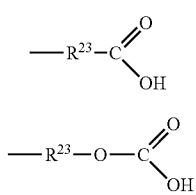

Formula X

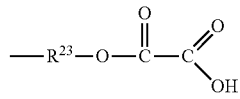

Formula XI

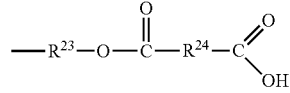

Formula XII $R^{23}$ may be a $C_{1-5}$ group, e.g. a $C_{1-5}$ alkyl group, a $C_{1-5}$alkenyl group, a $C_{1-5}$alkynyl group, or an amide-containing $C_{1-5}$ group, or $R^{23}$ may be absent. Preferably $R^{23}$ is linear. E.g. in one embodiment of the compound according to formula IX, $R^{23}$ is absent and thus group A consists of a carboxylic acid group. $R^{24}$ in formula IX may be a $C_{1-5}$ group, e.g. a $C_{1-5}$ alkyl group, a $C_{1-5}$alkenyl group, a $C_{1-5}$alkynyl group, or an amide-containing $C_{1-5}$ group.

In another embodiment, the acidic group comprised within group A is a sulfonic acid. For example, group A may be a sulfonic acid group according to formula XIII:

Formula XIII
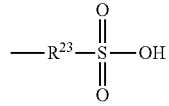

$R^{23}$ may be a $C_{1-5}$ group, e.g. a $C_{1-5}$ alkyl group, a $C_{1-5}$alkenyl group, a $C_{1-5}$alkynyl group, or an amide-containing $C_{1-5}$ group, or $R^{23}$ may be absent. Preferably $R^{23}$ is linear. E.g. in one embodiment of the compound according to formula XIII, $R^{23}$ is absent and thus group A consists of a sulfonic acid group.

In another embodiment, the acidic group comprised within group A is a sulfuric acid monoester. For example, group A may be a sulfuric acid monoester group according to formula XIV:

Formula XIV
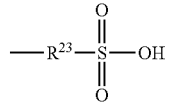

$R^{23}$ may be a $C_{1-5}$ group, e.g. a $C_{1-5}$ alkyl group, a $C_{1-5}$alkenyl group, a $C_{1-5}$alkynyl group, or an amide-containing $C_{1-5}$ group, or $R^{23}$ may be absent. Preferably $R^{23}$ is linear. E.g. in one embodiment of the compound according to formula XIV, $R^{23}$ is absent and thus group A consists of a sulfuric acid monoester group.

In another embodiment, the acidic group comprised within group A is a sulfonamide. For example, group A may be a sulfonamide group according to formula XV:

Formula XV
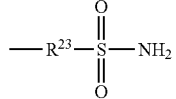

$R^{23}$ may be a $C_{1-5}$ group, e.g. a $C_{1-5}$ alkyl group, a $C_{1-5}$alkenyl group, a $C_{1-5}$alkynyl group, or an amide-containing $C_{1-5}$ group, or $R^{23}$ may be absent. Preferably $R^{23}$ is linear. E.g. in one embodiment of the compound according to formula XV, $R^{23}$ is absent and thus group A consists of a sulfonamide group.

In another embodiment, the acidic group comprised within group A is a phosphonic acid. For example, group A may be a phosphonic acid group according to formula XVI or a phosphonic acid monoester group according to formula XVII:

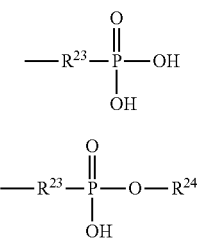

Formula XVI

Formula XVII $R^{23}$ may be a $C_{1-5}$ group, e.g. a $C_{1-5}$ alkyl group, a $C_{1-5}$alkenyl group, a $C_{1-5}$alkynyl group, or an amide-containing $C_{1-5}$ group, or $R^{23}$ may be absent. Preferably $R^{23}$ is linear. E.g. in one embodiment of the compound according to formula XVI, $R^{23}$ is absent and thus group A consists of a phosphonic acid group. $R^{24}$ may be a $C_{1-18}$ group e.g. a $C_{1-18}$alkyl group, a $C_{1-18}$ alkenyl group, a $C_{1-18}$alkynyl group, an amide-containing $C_{1-18}$ group, or an aryl group. In particular the aryl group may be a phenyl group, e.g. $R^{24}$ may be a phenyl group having substituents $R^{18}$, $R^{19}$ and $R^{20}$, as defined in formula I.

In another embodiment, the acidic group comprised within group A is a phosphoric acid. For example, group A may be a phosphoric acid monoester group according to formula XVIII or a phosphoric acid diester group according to formula XIX, or a polyphosphoric acid group according to formula XX:

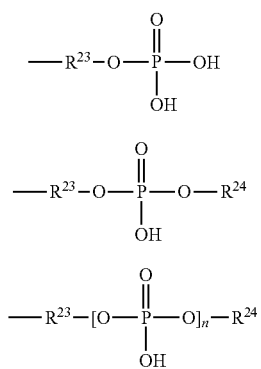

Formula XVIII

Formula XIX

Formula XX $R^{23}$ may be a $C_{1-5}$ group, e.g. a $C_{1-5}$ alkyl group, a $C_{1-5}$alkenyl group, a $C_{1-5}$alkynyl group, or an amide-containing $C_{1-5}$ group, or $R^{23}$ may be absent. Preferably $R^{23}$ is linear. E.g. in one embodiment of the compound according to formula XVIII, $R^{23}$ is absent and thus group A consists of a phosphoric acid monoester group. In one embodiment of the compound according to formula XIX, $R^{23}$ is absent and thus group A consists of a phosphoric acid diester group. $R^{24}$ may be a $C_{1-18}$ group e.g. a $C_{1-18}$alkyl group, a $C_{1-18}$alkenyl group, a $C_{1-18}$alkynyl group, an amide-containing $C_{1-18}$ group, or an aryl group. In particular the aryl group may be a phenyl group, e.g. $R^{24}$ may be a phenyl group having substituents $R^{18}$, $R^{19}$ and $R^{20}$, as defined in formula I.

In another embodiment, the acidic group comprised within group A is an arsenic acid. For example, group A may be a group according to formula XVI, XVII, XIII, XIX or XX, wherein the phosphorus atom has been replaced by an arsenic atom (As).

In another embodiment, the acidic group comprised within group A is a sulfinic acid. For example, group A may be a sulfinic acid group according to formula XXI:

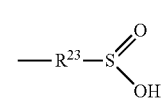

Formula XXI $R^{23}$ may be a $C_{1-5}$ group, e.g. a $C_{1-5}$ alkyl group, a $C_{1-5}$alkenyl group, a $C_{1-5}$alkynyl group, or an amide-containing $C_{1-5}$ group, or $R^{23}$ may be absent. Preferably $R^{23}$ is linear. E.g. in one embodiment of the compound according to formula XXI, $R^{23}$ is absent and thus group A consists of a sulfinic acid group.

In another embodiment, the acidic group comprised within group A is a thiocarboxylic acid. For example, group A may be a thiocarboxylic acid group according to formula XXII or formula XXIII:

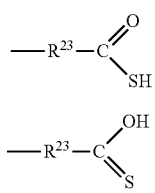

Formula XXII

Formula XXIII $R^{23}$ may be a $C_{1-5}$ group, e.g. a $C_{1-5}$ alkyl group, a $C_{1-5}$alkenyl group, a $C_{1-5}$alkynyl group, or an amide-containing $C_{1-5}$ group, or $R^{23}$ may be absent. Preferably $R^{23}$ is linear. E.g. in one embodiment of the compound according to formula XXII or formula XXIII, $R^{23}$ is absent and thus group A consists of a thiocarboxylic acid group.

In one embodiment, group A of formula I is phosphoric acid mono- or diester group, e.g. a group —$R^{23}$—(HPO$_4$)—$R^{24}$ according to formula XIX, wherein $R^{23}$ is absent or an alkyl (e.g. $C_{1-18}$alkyl), branched alkyl, aryl, or substituted aryl, and $R^{24}$ is hydrogen or an alkyl (e.g. $C_{1-18}$ alkyl), branched alkyl, aryl, or substituted aryl.

In a further embodiment, the lipophilic compound comprises a compound of the Formula VIII:

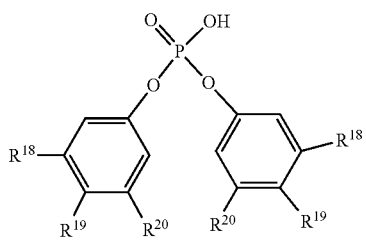

wherein $R^{18}$, $R^{19}$ and $R^{20}$ are as defined for Formula I. Preferably, the membrane comprises a salt of the lipophilic compound of Formula VIII.

In one embodiment, one of $R^{18}$, $R^{19}$ or $R^{20}$ is a $C_{4-18}$alkyl group as defined above (i.e. a $C_{4-18}$alkyl group which is linear at positions 1, 2 and 3, counting from the phenyl group, or in total only has one side chain at said positions 1, 2 and 3) and the others are, independently, hydrogen or a linear $C_{1-18}$ alkyl group.

In a further embodiment, one of $R^{18}$, $R^{19}$ or $R^{20}$ is a $C_{4-18}$alkyl group as defined above and the others are hydrogen. In a further embodiment, $R^{19}$ is a $C_{4-18}$alkyl group as defined above and $R^{18}$ and $R^{20}$ are hydrogen.

In one embodiment, said $C_{4-18}$alkyl group(s) is/are linear. In another embodiment, said $C_{4-18}$alkyl group(s) comprise(s) at least 6, such as at least 8 carbon atoms, e.g. 8, 9, 10, 11 or 12 carbon atoms.

In a further embodiment, only one of $R^{18}$, $R^{19}$ or $R^{20}$ is a $C_{4-18}$alkyl group, and said $C_{4-18}$ alkyl group comprises at least 6, such as at least 8 carbon atoms, e.g. 8, 9, 10, 11 or 12 carbon atoms.

In a preferred embodiment, the lipophilic compound comprises a compound of the formula VIII wherein $R^{18}$ and $R^{20}$ are hydrogen and $R^{19}$ is an octyl group.

In a preferred embodiment, the lipophilic compound is provided in the form of a salt. Preferred salts are magnesium salt and calcium salts.

In a preferred embodiment, the lipophilic compound is hemi-calcium bis[4-octylphenyl]phosphate, hemi-magnesium bis[4-octylphenyl]phosphate or a mixture of these two salts.

Lipophilic compounds, such as hemi-calcium bis[4-octylphenyl]phosphate and hemi-magnesium bis[4-octylphenyl]phosphate, may be prepared by standard methods known in the art.

In a preferred embodiment, the lipophilic salt is a mixture of hemi-calcium bis[4-octylphenyl]phosphate and hemi-magnesium bis[4-octylphenyl]phosphate, wherein the mixture contains at least 50% hemi-magnesium bis[4-octylphenyl]phosphate, such as at least 80% hemi-magnesium bis [4-octylphenyl]phosphate, e.g. between 80% and 90% hemi-magnesium bis[4-octylphenyl]phosphate.

In a further preferred embodiment of the magnesium ion selective membrane of the invention, the ionophore is 4,7-diundecyl-1,10-phenanthroline and the lipophilic salt is a mixture of hemi-magnesium bis[4-octylphenyl]phosphate and hemi-calcium bis[4-octylphenyl]phosphate.

In a preferred embodiment, the molar ratio between the ionophore and the lipophilic compound or the anion(s) of the lipophilic salt(s) is between 2:1 and 1:1, such as a molar ratio between 1.8:1 and 1.2:1.

Besides the lipophilic compounds and lipophilic salts mentioned above, further salts may be present in the membrane of the invention. Thus, in embodiment, the membrane of the invention comprises a further salt, such as tetrakis(4-chlorophenyl)borate salt.

Ionophores Comprising a Covalently Linked Acidic Group

In a further aspect of the invention, the ionophore and the acidic group are covalently linked rather than part of separate compounds.

Accordingly, in a main aspect, the invention relates to a magnesium ion selective membrane comprising:
  an ionophore covalently linked to an acidic group via a spacer, wherein said spacer comprises at least one carbon atom, or
  a salt of said ionophore covalently linked to an acidic group via a spacer.

In a preferred embodiment, the ionophore is lipophilic.

In one embodiment, said spacer is an alkyl group, such as a linear or branched alkyl group having a total of from 1 to 18 carbon atoms, wherein the alkyl group optionally is substituted. In another embodiment, said spacer a linear alkyl group, e.g. a —$(CH_2)_n$—group, wherein n is at least 1, such as 1, 2, 3, 4 or 5, or at least 2.

In one embodiment, said ionophore is a phenanthroline compound which is 1,10-phenanthroline or a substituted form thereof. In one embodiment hereof, the spacer is covalently linked to the phenanthroline compound at the carbon atom at position 2, 3, 4, 5, 6, 7,8 or 9 of 1,10-phenanthroline.

In a further embodiment, the ionophore covalently linked to an acidic group via a spacer (wherein said spacer comprises at least one carbon atom) is a phenanthroline compound of the formula II:

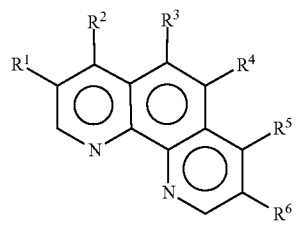

wherein each of $R^1$-$R^6$ is any of:
H;
any of F, Cl, Br, I, $NO_2$, CN, or $CF_3$;
$C_{1-18}$ alkyl;
$C_{1-18}$ aryl;
$C_{1-18}$ alkenyl;
$(CH_2)_m Y$, wherein m is 0 or an integer from 1 to 4, Y is any of —$OR^7$, —$NR^7R^8$, —$OCOR^7$, —$NR^7COR^8$, —$COR^7$, —$COOR^7$, —$SO_3R^7$, —$OSiR^7R^8R^9$, —$PO_4R^7R$, —$PO_3R^7R^8$, wherein each of $R^7$, $R^8$, and $R^9$ are any of H, alkyl, branched alkyl, aryl, or substituted aryl;
$C_n$—$R^{10}R^{11}$, wherein n is 0 or an integer between 1 and 17 inclusive, $R^{10}$ is C, N, NCO, or $CH_2$—Z—$CH_2$ wherein Z is any of O, NH, S, OCO, or CO, $R^{11}$ is

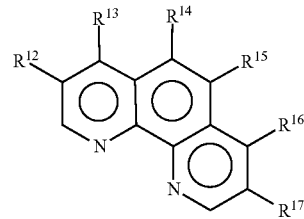

and $R^{11}$ is linked to $R^{10}$ at any of positions 3, 4, 5, 6, 7, or 8 of $R^{11}$, $R^{12}$-$R^{17}$ are any of H, $C_{1-18}$ alkyl, $C_{1-18}$ aryl, or deleted, provided that if $R^{11}$ is linked to $R^{10}$ at position 3 of $R^{11}$ then $R^{12}$ is deleted, if $R^{11}$ is linked to $R^{10}$ at position 4 of $R^{11}$ then $R^{13}$ is deleted, if $R^{11}$ is linked to $R^{10}$ at position 5 of $R^{11}$ then $R^{14}$ is deleted, if $R^{11}$ is linked to $R^{10}$ at position 6 of $R^{11}$ then $R^{15}$ is deleted, if $R^{11}$ is linked to $R^{10}$ at position 7 of $R^{11}$ then $R^{16}$ is deleted, if $R^{11}$ is linked to $R^{10}$ at position 8 of $R^{11}$ then $R^{17}$ is deleted;

provided that one of $R^1$-$R^6$ is other than H and that each of the C atoms at positions 2 and 9 of the 1,10-phenanthroline is bonded, by the bond which does not participate in the fused ring structure, to an H, and
wherein one of $R^1$ to $R^6$ comprises the spacer and the acidic group, preferably wherein $R^1$ or $R^6$ comprises the spacer and the acidic group.

In a further embodiment hereof, $R^1$ to $R^6$ include a total of at least 6 carbon atoms, e.g. 6, 7, 8, 9 10 or 11 carbon atoms, such as a total of at least 11 carbon atoms, e.g. between 11 and 18 carbon atoms.

In another embodiment, one or more of $R^1$, $R^2$, $R^3$, $R^4$, $R^5$ and $R^6$ is an alkyl or aryl group having between 1 and 18 carbon atoms. For example, one or two groups selected from $R^1$, $R^2$, $R^3$, $R^4$, $R^5$ and $R^6$ may be an alkyl or aryl group having between 1 and 18 carbon atoms and the others are hydrogen, e.g. $R^1$ and $R^2$, $R^1$ and $R^3$, $R^1$ and $R^4$, $R^1$ and $R^5$, $R^1$ and $R^6$, $R^2$ and $R^3$, $R^2$ and $R^4$, $R^2$ and $R^5$, $R^2$ and $R^6$, $R^3$ and $R^4$, $R^3$ and $R^5$, $R^3$ and $R^6$, $R^4$ and $R^5$, $R^4$ and $R^6$ or $R^5$ and $R^6$ are alkyl or aryl groups having between 1 and 18 carbon atoms and the others are hydrogen.

In another embodiment, one or more of $R^1$, $R^2$, $R^3$, $R^4$, $R^5$ and $R^6$ is an alkyl group having between 1 and 18 carbon atoms. For example, one or two groups selected from $R^1$, $R^2$, $R^3$, $R^4$, $R^5$ and $R^6$ may be an alkyl group having between 1 and 18 carbon atoms and the others are hydrogen, e.g. $R^1$ and $R^2$, $R^1$ and $R^3$, $R^1$ and $R^4$, $R^1$ and $R^5$, $R^1$ and $R^6$, $R^2$ and $R^3$, $R^2$ and $R^4$, $R^2$ and $R^5$, $R^2$ and $R^6$, $R^3$ and $R^4$, $R^3$ and $R^5$, $R^3$ and $R^6$, $R^4$ and $R^5$, $R^4$ and $R^6$ or $R^5$ and $R^6$ are alkyl groups having between 1 and 18 carbon atoms and the others are hydrogen.

In another embodiment, one or more of $R^1$, $R^2$, $R^3$, $R^4$, $R^5$ and $R^6$ is an alkyl group having between 6 and 18 carbon atoms. For example, one or two groups selected from $R^1$, $R^2$, $R^3$, $R^4$, $R^5$ and $R^6$ may be an alkyl group having between 6 and 18 carbon atoms and the others are hydrogen, e.g. $R^1$ and $R^2$, $R^1$ and $R^3$, $R^1$ and $R^4$, $R^1$ and $R^5$, $R^1$ and $R^6$, $R^2$ and $R^3$, $R^2$ and $R^4$, $R^2$ and $R^5$, $R^2$ and $R^6$, $R^3$ and $R^4$, $R^3$ and $R^5$, $R^3$ and $R^6$, $R^4$ and $R^5$, $R^4$ and $R^6$ or $R^5$ and $R^6$ are alkyl groups having between 6 and 18 carbon atoms and the others are hydrogen.

In another embodiment, one of $R^1$, $R^2$, $R^3$, $R^4$, $R^5$ and $R^6$ is an alkyl group having between 1 and 18 carbon atoms, such as between 6 and 18 carbon atoms, e.g. between 11 and 18 carbon atoms.

In another embodiment, $R^2$ and/or $R^5$ is an alkyl group having between 1 and 18 carbon atoms, such as between 6 and 18 carbon atoms, e.g. between 11 and 18 carbon atoms.

In another embodiment, $R^2$ and/or $R^5$ is an aryl group having between 1 and 18 carbon atoms.

In a preferred embodiment, the phenanthroline compound is 4-undecyl-1,10-phenanthroline covalently linked to an acidic group via a spacer, wherein said spacer comprises at least one carbon atom, such as two or three carbon atoms.

In another preferred embodiment, the phenanthroline compound is 4,7-diundecyl-1,10-phenanthroline covalently linked to an acidic group via a spacer, wherein said spacer comprises at least one carbon atom.

Preferably, the spacer comprises 1 to 18 carbon atoms. In one embodiment, the spacer comprises at least 2, such as at least 3 carbon atoms, and the spacer is covalently linked at position 2, 3, 4, 5, 6, 7, 8 or 9 of the 1,10-phenanthroline compound.

In one embodiment, the acidic group is selected from the group consisting of: a carboxylic acid, a sulfonic acid, a sulfuric acid monoester, a sulfonamide, a phosphonic acid, a phosphoric acid, an arsenic acid, a sulfinic acid or a thiocarboxylic acid.

In a preferred embodiment, the acidic group is —(HPO$_4$)$R^7$, —(HPO$_3$)$R^7$, wherein $R^7$ is H, alkyl, branched alkyl, aryl, or substituted aryl, e.g. 4-octylphenyl.

In another embodiment, the ionophore has a tripodal stereochemical structure, such as one of the structures depicted in Formulas IV, V, VI and VII. In one further embodiment hereof, the acidic group is positioned distal of the malondiamide group on one, two or three arms of the structure depicted in Formula IV, V, VI or VII. "Distal" in this context means distal relative to the center of the tripodal structure. Preferably, only one arm of the molecule has a covalently bound acidic group. In another embodiment, in one of the three arms of the structure depicted in Formulas IV, V, VI or VII, the malondiamide group is partially or entirely replaced by the acidic group.

Further Membrane Components

Plasticizers—The membranes of the invention typically further comprise a plasticizer. The role of the plasticizer is to keep other components, such as the ionophore, solvated. Many suitable plasticizers, e.g. esters, phosphonates and ethers, have been described in the art. In one embodiment, the plasticizer is as 4-hexylphenyl 2-nitrophenyl ether (NHPE) or 2-nitrophenyl octyl ether (NPOE) or a mixture thereof. In one embodiment, the plasticizer, such as NHPE, constitutes about 40% to 80% of the dry membrane mass, e.g. between 50% and 70% of the dry membrane mass, such as between 55% and 65% of the dry membrane mass.

Polymers—The membranes of the invention typically further comprise a polymer or a mixture of polymers, a polymer blend. Polymers give the membrane structural integrity as they provide a network to contain the plasticizer and the active components. Non-limiting examples of polymers and co-polymers that may be used include poly(vinyl chloride), carboxylated poly(vinyl chloride), polyurethane, poly(vinyl chloride-co-vinyl acetate), poly(vinyl chloride-co-vinyl alcohol), poly(vinyl chloride-co-vinyl acetate-co-vinyl alcohol) and combinations of any of these.

In a preferred embodiment, the membrane comprises a polymer blend, wherein said polymer blend comprises:
1. a first polymer which is carboxylated poly(vinyl chloride) or poly(vinyl chloride), wherein the molecular weight of said first polymer is from 100,000 to 500,000, and
2. a second polymer, which is a co-polymer of vinyl chloride and at least one further monomer group having a hydrophilic group, wherein the molecular weight of said second polymer is below 100,000,
wherein, if said first polymer is carboxylated poly(vinyl chloride), said second polymer has more hydrophilic groups than said first polymer.

In one embodiment, said first polymer is carboxylated poly(vinyl chloride). In a further embodiment, said first polymer is carboxylated poly(vinyl chloride) and said second polymer has at least 1.5-fold more hydrophilic groups than said first polymer, such as at least 2-fold, e.g. at least 4-fold, such as at least 5-fold, e.g. at least 10-fold more hydrophilic groups than said first polymer. In an even further embodiment, said first polymer is carboxylated poly(vinyl chloride) and said carboxylated poly(vinyl chloride) is between 0.1% and 10% carboxylated, e.g. between 0.5% and 5% carboxylated, such as between 1% and 3% carboxylated, e.g. 1.8% carboxylated.

In another embodiment, said first polymer is poly(vinyl chloride).

In one embodiment, the molecular weight of said first polymer is at least 110,000, e.g. at least 120,000, such as between 130,000 and 400,000, e.g. between 130,000 and 300,000, e.g. between 130,000 and 250,000.

In one embodiment, said first polymer is carboxylated poly(vinyl chloride) and the molecular weight of said first polymer is at least 110,000, e.g. at least 120,000, such as between 130,000 and 400,000, e.g. between 200,000 and 300,000, e.g. between 200,000 and 250,000, e.g. 220,000.

In another embodiment, said first polymer is poly(vinyl chloride) and the molecular weight of said first polymer is at least 110,000, e.g. at least 120,000, such as between 120,000 and 200,000, e.g. between 130,000 and 160,000, e.g. 140,000.

In one embodiment of the membrane of the invention, said further monomer in the second polymer is vinyl alcohol, a vinyl ester or a hydroxy-functional acrylate. In a further embodiment, said second polymer is a co-polymer of vinyl chloride, vinyl acetate, vinyl alcohol and, optionally, a further monomer comprising a hydrophilic group, such as acrylic acid, methacrylic acid or maleic acid.

In an even further embodiment, said second polymer is poly(vinyl chloride-co-vinyl acetate-co-vinyl alcohol). In one embodiment, said poly(vinyl chloride-co-vinyl acetate-co-vinyl alcohol) comprises between 75% and 98% vinyl chloride, such as between 85% and 95% vinyl chloride, e.g. between 89% and 93% vinyl chloride, such as 91% vinyl chloride. In another embodiment, said poly(vinyl chloride-co-vinyl acetate-co-vinyl alcohol) comprises between 1% and 20% vinyl acetate, such as between 1% and 10% vinyl acetate, e.g. between 1% and 5% vinyl acetate, such as 3% vinyl acetate. In a further embodiment, said poly(vinyl chloride-co-vinyl acetate-co-vinyl alcohol) comprises between 1% and 15% vinyl alcohol, such as between 1% and 10% vinyl alcohol, e.g. between 4% and 8% vinyl alcohol, such as 6% vinyl alcohol.

In one embodiment, the molecular weight of the second polymer is less than 100,000, e.g. between 30,000 and 90,000, preferably between 60,000 and 80,000, such as 70,000.

In one embodiment, the ratio of the first polymer mass to the second polymer mass in the membrane is between 10:1 and 1:5, e.g. between 4:1 and 1:4, such as between 2:1 and 1:3, e.g. between 2:3 and 3:7, such as 1:2.

In one embodiment, said first polymer is carboxylated poly(vinyl chloride) and the ratio of the first polymer mass to the second polymer mass in the membrane is between 4:1 and 1:4, such as between 2:1 and 1:3, e.g. between 3:2 and 3:7, or between 2:3 and 3:7 such as 1:2.

In another embodiment, said first polymer is poly(vinyl chloride) and the ratio of the first polymer mass to the second polymer mass in the membrane is between 10:1 and 1:5, such as between 7:1 and 1:2, e.g. between 5:1 and 1:2, such as between 5:1 and 2:3, e.g. between 5:1 and 2:1, such as 4:1.

In one embodiment, the polymer blend constitutes about 10% to 50% of the dry membrane mass (i.e. the mass of the components before mixing in solvent), e.g. between 20% and 40% of the dry membrane mass, such as between 25% and 35% of the dry membrane mass, e.g. between 25% and 30% of the dry membrane mass. In a preferred embodiment, the membrane has the composition specified in Table 1 below.

TABLE 1

Wet and dry mass composition of the mixed membrane solution.

| Component | Wet mass (%) | Dry mass (%) |
|---|---|---|
| Hemi-Mg-bis-[4-octylphenyl]phosphate | 1.49 | 4.58 |
| Hemi-Ca-bis-[4-octylphenyl]phosphate | 0.26 | 0.81 |
| 4,7-Diundecyl-1,10-phenanthroline (DUP) | 2.41 | 7.40 |
| 1.8% carboxylated PVC | 3.07 | 9.42 |
| PVC co-Polymer* | 6.15 | 18.89 |
| 4-hexylphenyl 2-nitrophenyl ether (NHPE) | 19.17 | 58.90 |
| Cyclohexanone, Sigma C102180 | 67.46 | |

*poly(vinyl chloride-co-vinyl acetate-co-vinyl alcohol) having a content of 91% vinyl chloride, 3% vinyl acetate and 6% vinyl alcohol.

Process for Preparing Membranes of the Invention

In a further aspect, the invention relates to a process for preparing a magnesium ion selective membrane of the invention by mixing the components in a solvent, dispensing the resulting solution on a desired support and allowing the solvent to evaporate. Any suitable solvent may be used. In one embodiment, the solvent is cyclohexanone. The support may be flexible or rigid. The support is preferably made of non-conducting material such as silicon, polymer, a printed circuit board (PCB), flex-PCB, polyethylene terephthalate (PET), polyimide (PI), ceramic, alumina, glass, wood product, frit, etc.

Electrodes and Potentiometric Sensors

In a further main aspect, the invention relates to an ion-selective electrode comprising the magnesium ion selective membrane of the invention as described herein. The electrode may be made on a support by using thick film approach e.g. screen printing, rotogravure, pad printing, stenciling conductive material such as carbon, Cu, Pt, Pd, Au, and/or nanotubes, etc. or by using thin film approach e.g. by sputtering, thermal spraying and/or cold spraying conductive material. The support may be flexible or rigid. The support is preferably made of non-conducting material such as silicon, polymer, a printed circuit board (PCB), flex-PCB, polyethylene terephthalate (PET), polyimide (PI), ceramic, alumina, glass, wood product, frit, etc.

In an even further main aspect, the invention relates to a sensor assembly where two or more analyte electrodes are present on a single support with or without a reference electrode (see e.g. U.S. Pat. No. 5,916,425 for a sensor assembly including a reference electrode). In some embodiments, the sensor assembly is made of two supports each comprising two or more analyte electrodes with or without a reference electrode. The supports may be placed in a layered structure on top of each other such that the surfaces of said supports with the electrodes are facing each other (see e.g. WO2008/131767). Alternative suitable sensor assemblies have been described in WO2018/112017, WO2018/112012, WO2018/112008, WO2017/120464, WO2017/019609, WO2016/106320, WO2016/011308, WO2016/007716 and WO2013/163120.

In one embodiment, the system is calibrated with calibrators containing physiological concentrations of potentially interfering compounds ($Ca^{2+}$, $K^+$ and $Na^+$).

In some embodiments, the system contains one or more electrodes for measurement of other cations, e.g. calcium ions, so that interference can be minimized by chemometric correction of the analyte signal based on measurements of the activity of the cations.

Uses and Methods of Use

As described above, in a further main aspect, the invention relates to the use of a potentiometric sensor or electrode according to the invention for the determination of the magnesium ion concentration in a sample.

Similarly, the invention relates to a method of determining the magnesium ion concentration of a liquid sample comprising contacting said sample with an electrode according to the invention or a potentiometric sensor according to the invention and determining the magnesium ion concentration based on signal provided by said electrode or potentiometric sensor.

A biological sample tested for the presence of an analyte may be a physiological fluid such as diluted or undiluted whole blood, serum, plasma, saliva, urine, feces, pleura, cerebrospinal fluid, synovial fluid, milk, ascites fluid, peritoneal fluid or amniotic fluid.

Examples of other biological samples include fermentation broths, microbial cultures, waste water, food products and the like.

In a preferred embodiment, the sample is a blood sample or a serum sample. A sample, such as a blood sample, a serum sample, a plasma sample or a pleural sample can e.g. be a sample from a human subject.

The purpose of determining the magnesium ion levels may e.g. be to diagnose a disease or disorder in a patient, such as a human patient, or to monitor magnesium levels in a patient undergoing, or being enrolled for a treatment, such as medical therapy or surgery. In one embodiment, the disease or disorder is a cardiovascular disease or disorder. In another embodiment, the sample is a sample from a newborn, i.e. an infant of less than 28 days old.

Zhang (2011) Am J Biomed Sci 3:301 summarizes a number of studies which demonstrate an association between magnesium levels, in particular hypomagnesemia, and clinical outcomes. For example, studies have demonstrated association of hypomagnesemia and mortality rates in ICU patients experiencing hemodialysis, type 2 diabetes, cardiovascular diseases, or medical surgical intensive care. Furthermore, in heart disease patients, magnesium deficiency has been found to contribute to coronary vasospasm, arrhythmias, fibrillation, infarction, and sudden death. A study on magnesium intervention during cardiopulmonary bypass operations showed that intraoperative correction of iMg is associated with a reduction in postoperative ventricular arrhythmia and maintenance of an uninterrupted sinus rhythm. Clinical trial results also suggest a benefit for magnesium therapy for acute stroke patients in the ambulance or emergency department within the first two hours of the onset of stroke symptoms. Magnesium monitoring is also advocated in preeclampsia, a condition reported to be linked with hypomagnesemia and which occurs in 5-7% of pregnancies in Europe and the USA. Other findings have suggested that the ratio of iCa:iMg is a crucial diagnostic parameter for prevention of vascular and neurological complications in preeclampsia-eclampsia patients. Soliman et al. (2003) Crit. Care Med. 31:1082 reported a correlation between the onset of ionized hypomagnesemia during ICU stays and high morbidity and mortality rates.

Thus, in further embodiments, the sample in which the magnesium ion level is determined in the method or use according to the invention, may e.g. be a sample from a patient in acute admission or from a patient undergoing, or enrolled for, medical therapy or surgery, such as cardiac surgery, e.g. a cardiopulmonary bypass operation. In further embodiments, the sample is from a patient with poor food intake, a malabsorption disorder, hypokalemia, hypocalcemia, alcoholism or from a patient taking diuretics or other drugs associated with hypomagnesemia. In further embodiments, the sample is from a patient having renal disease, hypertension, preeclampsia, diabetes mellitus, diabetic ketoacidosis, arrhythmia, sepsis, chest pain, acute stroke, trauma chock, burns/smoke inhalation, acute lung diseases or a cardiac disease, such as cardiac arrest. In another embodiment, the patient is a patient at the maternity ward or a patient undergoing haemodialysis. Furthermore, the sample may be from an ICU patient experiencing hemodialysis, type 2 diabetes, cardiovascular diseases, or medical surgical intensive care.

The present invention is further illustrated by the following examples, which should not be construed as limiting the scope of the invention.

EXAMPLES

Example 1: Preparation of Ion Selective Membranes

A stock solution of hemi-magnesium bis[4-octylphenyl] phosphate (MgOPP) was prepared by mixing MgOPP and cyclohexanone (>99.8%) in a ratio of 48.28 grams of cyclohexanone per gram of MgOPP. The compounds were mixed at room temperature and subsequently stirred in the dark for a minimum of 8 hours at room temperature or stirred for a minimum of 4 hours at 37° C.

A membrane dispensing solution was prepared by mixing the following components:

| Compound | Quantity |
| --- | --- |
| hemi-calcium bis[4-octylphenyl]phosphate | 0.00263 ± 2% |
| 4,7-diundecyl-1, 10-phenanthroline | 0.02410 ± 2% |
| Poly(vinyl chloride-co-acrylic acid (carboxylated PVC - 1.8% carboxyl basis - MW ~220,000 | 0.03073 ± 1.5% |
| Poly(vinyl chloride-co-vinyl acetate-co-vinyl alcohol) - PVC co-polymer containing 3% of vinyl acetate and 6% of vinyl alcohol - Mr ~24,500 (Fluka 27827) | 0.06148 ± 1.5% |
| 4-hexylphenyl 2-nitrophenyl ether (NHPE) | 0.19173 ± 1.5% |
| MgOPP stock solution in cyclohexanone | 0.68932 ± 0.5% |

The compounds were mixed in vials filled with argon or nitrogen gas at room temperature and subsequently stirred in the dark for a minimum of 40 hours at room temperature or stirred for a minimum of 16 hours at 37° C. The resulting solution was used for dispensing membranes onto a poly(3, 4-ethylenedioxythiophene)-poly(styrenesulfonate)-(PEDOT-) covered gold electrode on a ceramic support. The solvent was subsequently allowed to evaporate to obtain the plasticized ion selective membrane.

Example 2: Performance of Membranes Comprising Lipophilic Salts

Two membranes containing a phenanthroline-based ionophore and a lipophilic tetrakis borate salt were prepared in order to study the effect of the addition of a lipophilic acid salt on membrane performance. The lipophilic acid salts tested were hemi-calcium bis[4-octyl phenyl]phosphate and hemi-calcium-bis[4-(1,1,3,3-tetramethyl butyl)-phenyl] phosphate.

Two membranes were prepared as described in Example 1, except that the compositions were as follows.

| Membrane 1 Compounds | Quantity (g) |
|---|---|
| hemi-calcium bis[4-octylphenyl]phosphate | 0.00302 |
| 4,7-diundecyl-1, 10-phenanthroline | 0.00900 |
| Poly(vinyl chloride) | 0.02763 |
| Poly(vinyl chloride-co-vinyl acetate-co-vinyl alcohol) - PVC co-polymer containing 3% of vinyl acetate and 6% of vinyl alcohol | 0.00707 |
| 4-hexylphenyl 2-nitrophenyl ether (NHPE) | 0.07299 |
| Potassium tetrakis-(4-chlorophenyl) borate | 0.00201 |

| Membrane 2 Compounds | Quantity |
|---|---|
| hemi-calcium-bis[4-(1, 1,3,3-tetramethylbutyl)-phenyl]phosphate 4,7-diundecyl-1, 10-phenanthroline | 0.00398 |
| | 0.00982 |
| Poly(vinyl chloride) | 0.02770 |
| Poly(vinyl chloride-co-vinyl acetate-co-vinyl alcohol) - PVC co-polymer containing 3% of vinyl acetate and 6% of vinyl alcohol 4-hexylphenyl 2-nitrophenyl ether (NHPE) | 0.00703 |
| | 0.07364 |
| Potassium tetrakis-(4-chlorophenyl) borate | 0.00203 |

Each membrane was dispensed onto three individual electrodes of an electrode array, which also contained a $Ca^{2+}$ ion selective electrode. The membranes were dispensed as described in Example 1 except that a vanadium bronze was used as a transducer material instead of PEDOT. The resulting arrays of ion selective electrodes were placed into a measuring chamber in a test analyzer. The measuring chamber had fluidic contact with a reference electrode. The test analyzer was programmed for automatic control of liquid transport of calibration and rinse solutions, aspiration of samples, sampling of the potentiometric signal of each electrode position, and data acquisition thereof.

The $Mg^{2+}$ ion selective electrodes were calibrated using three calibration solutions containing $Mg^{2+}$ and $Ca^{2+}$ ions in three different ratios. Status value (E0), sensitivity (S) and selectivity coefficient (K) for $Mg^{2+}$ ions over $Ca^{2+}$ ions, were determined based on the electrode signals obtained on the calibration solution. The $Ca^{2+}$ ion selective electrode was also calibrated. The calibrated sensors were then subjected to measurements on:

Five aqueous samples spanning a concentration range of $Mg^{2+}$ ions from 0.1 mM to 2.5 mM.

Whole blood from a healthy donor. Five repetitive measurements on the same sample were conducted. The concentration of $Mg^{2+}$ ions in the sample was also determined by measurements on a NOVA 8 analyzer from NOVA Biomedical.

Low and high concentrations of possible interferent $Zn^{2+}$ ions: 0 µM, 20 µM and 200 µM, in solutions prepared with 5% bovine serum albumin (BSA) and a constant concentration of $Mg^{2+}$ ions of 0.5 mM corresponding to the normal physiological concentration in plasma.

For each $Mg^{2+}$ ion selective electrode, the concentration of $Mg^{2+}$ ions (cMg) in a sample was calculated from the signal obtained on that particular sample by utilizing the values of the calibration parameters (E0, S, and K) determined for the electrode prior to the sample measurement and the concentration of $Ca^{2+}$ ions determined with the $Ca^{2+}$ ion selective electrode. For calculation of ionic $Mg^{2+}$ concentrations, the Nicolsky-Eisenman (NE) equation was used as sensor response model in accordance with IFCC guidelines (Ben Rayana et al. (2008) Clin Chem Lab Med 46(1):21). No corrections were subsequently applied to obtain the listed cMg values.

TABLE 2 cMg [mM] in aqueous samples with different concentrations of $Mg^{2+}$ ions measured with ion selective electrodes prepared with membrane 1 (cMg_1a-c) or membrane 2 (cMg_2a-b).

| Sample | cMg_1a | cMg_1b | cMg_1c | cMg_2a | cMg_2b | cMg_2c | Mean (cMg_1a-c) | Mean (cMg_2a-c) | Std (cMg_1a-c) | Std (cMg_2a-c) |
|---|---|---|---|---|---|---|---|---|---|---|
| 0.1 mM $Mg^{2+}$ | 0.127 | 0.125 | 0.125 | 0.122 | 0.129 | 0.120 | 0.125 | 0.124 | 0.001 | 0.005 |
| 0.2 mM $Mg^{2+}$ | 0.239 | 0.235 | 0.235 | 0.229 | 0.237 | 0.226 | 0.236 | 0.231 | 0.003 | 0.005 |
| 0.5 mM $Mg^{2+}$ | 0.546 | 0.543 | 0.540 | 0.531 | 0.535 | 0.514 | 0.543 | 0.527 | 0.003 | 0.012 |
| 1.0 mM $Mg^{2+}$ | 1.041 | 1.040 | 1.029 | 1.024 | 1.019 | 0.988 | 1.037 | 1.010 | 0.006 | 0.020 |
| 2.5 mM $Mg^{2+}$ | 2.489 | 2.477 | 2.462 | 2.470 | 2.444 | 2.387 | 2.476 | 2.434 | 0.014 | 0.042 |
| Slope | | 0.976 | | | 0.960 | | | | | |
| Intercept | | 0.044 | | | 0.040 | | | | | |
| R2 | | 1.000 | | | 0.999 | | | | | |

TABLE 3 cMg [mM] in a whole blood sample measured repetitively (rep#1-5) with ion selective electrodes prepared with membrane 1 (cMg_1a-c) or membrane 2 (cMg_2a-b), and when measured on a NOVA 8 analyzer from Nova Biomedical.

| Sample | cMg_1a | cMg_1b | cMg_1c | cMg_2a | cMg_2b | cMg_2c | cMg_NOVA8 |
|---|---|---|---|---|---|---|---|
| Whole blood (rep#1) | 0.682 | 0.678 | 0.677 | 0.964 | 0.950 | 0.979 | 0.630 |
| Whole blood (rep#2) | 0.690 | 0.688 | 0.684 | 0.959 | 0.948 | 0.987 | 0.610 |
| Whole blood (rep#3) | 0.685 | 0.683 | 0.676 | 0.934 | 0.917 | 0.944 | 0.610 |
| Whole blood (rep#4) | 0.686 | 0.683 | 0.682 | 0.928 | 0.913 | 0.950 | 0.600 |
| Whole blood (rep#5) | 0.684 | 0.683 | 0.680 | 0.951 | 0.926 | 0.955 | 0.620 |
| Mean | 0.685 | 0.683 | 0.680 | 0.947 | 0.931 | 0.963 | 0.614 |
| Std | 0.003 | 0.003 | 0.003 | 0.016 | 0.017 | 0.019 | 0.011 |

TABLE 4 cMg [mM] in aqueous samples with 0.5 mM $Mg^{2+}$, 5% BSA and different concentrations of $Zn^{2+}$,
measured with ion selective electrodes prepared with membrane 1 (cMg_1a-c) or membrane 2 (cMg_2a-b).

| Sample | cMg_1a | cMg_1b | cMg_1c | cMg_2a | cMg_2b | cMg_2c | Mean (cMg_1a-c) | Mean (cMg_2a-c) | Std (cMg_1a-c) | Std (cMg_2a-c) |
|---|---|---|---|---|---|---|---|---|---|---|
| 0 µM $Zn^{2+}$ | 0.508 | 0.529 | 0.505 | 0.776 | 0.760 | 0.794 | 0.514 | 0.777 | 0.013 | 0.017 |
| 20 µM $Zn^{2+}$ | 0.534 | 0.561 | 0.530 | 0.905 | 0.864 | 0.893 | 0.542 | 0.888 | 0.017 | 0.021 |
| 200 µM | 0.794 | 0.881 | 0.771 | 3.364 | 2.761 | 2.564 | 0.815 | 2.896 | 0.058 | 0.417 |

CONCLUSION

The membranes performed equally well with respect to measurements on aqueous samples with known concentration of $Mg^{2+}$ ions. However, membrane 1 had a lower deviation on blood samples than membrane 2 when compared to the cMg results readout by a NOVA 8 analyzer (Table 3 (0,685/0.685/0.68 deviating less from 0.614 than 0.947/0.931/0.963)). Also, less interference of zinc ions was observed for membrane 1 (Table 4 (values for membrane 1 (0.514/0.542/0.815) closer to 0.5 mM than the values for membrane 2 (0.777/0.888/2.896)).

Example 3: Performance of Membranes Comprising a Single Lipophilic Acid or Acid Salt Five membranes containing a phenanthroline-based ionophore and a single lipophilic salt were prepared in order to study the effect of the addition of a single lipophilic acid (or acid salt) on membrane performance. Four lipophilic acids (acid salts) were tested: hemi-Mx bis[4-octylphenyl]phosphate [Mx(OPP)$_2$] where Mx={calcium;magnesium}, 4-octylbenzoic acid (OBA), sodium 4-octylbenzenesulfonate (OBS) and sodium 4-dodecylbenzenesulfonate (DBS). A lipophilic salt used as standard in ion-selective electrodes was also tested: Potassium tetrakis-(4-chlorophenyl) borate.

The five membranes were prepared as described in Example 1, except that the compositions were as follows and that only Mg(OPP)$_2$ was pre-dissolved in the cyclohexanone before adding the remaining components. The compositions were made to ensure identical concentrations of lipophilic anions in the membranes.

| Membrane Compounds in Common for All Membrane IDs | Quantity (g) |
|---|---|
| 4,7-diundecyl-1, 10-phenanthroline | 0.2640 |
| Poly(vinyl chloride-co-acrylic acid (carboxylated PVC - 1.8% carboxyl basis - MW ~220,000 | 0.3360 |
| Poly(vinyl chloride-co-vinyl acetate-co-vinyl alcohol) - PVC co-polymer containing 3% of vinyl acetate and 6% of vinyl alcohol - Mr ~24,500 (Fluka 27827) | 0.6734 |
| 4-hexylphenyl 2-nitrophenyl ether (NHPE) | 2.1000 |
| Cyclohexanone | 7.2386 |

| Membrane ID | Lipophilic Salt | Quantity (g) |
|---|---|---|
| OPP | hemi-calcium bis[4-octylphenyl]phosphate [Ca(OPP)$_2$] | 0.0288 |
| | hemi-magnesium bis[4-octylphenyl]phosphate [Mg(OPP)$_2$] | 0.1514 |
| OBA | 4-octylbenzoic acid | 0.0867 |
| OBS | 4-octylbenzenesulfonate | 0.1089 |
| DBS | 4-dodecylbenzenesulfonate | 0.1289 |
| TETRAKIS | Potassium tetrakis-(4-chlorophenyl) borate | 0.1836 |

Each membrane was dispensed onto four identical electrodes each positioned on identical electrode arrays, which also contained a $Ca^{2+}$ ion selective electrode. The membranes were dispensed as described in Example 1. Each electrode array was placed into a measuring chamber in a test analyzer as described in Example 2.

The $Mg^{2+}$ ion selective electrodes were calibrated as described in Example 2, but in a more complex solution matrix suitable for a simultaneous calibration of other sensors, e.g. Na, K, Ca, Cl, pH, pO$_2$, pCO$_2$, Glucose and Lactate sensors. The $Ca^{2+}$ ion selective electrodes were also calibrated. The calibrated sensors were then subjected to measurements on:

SSM (Separate Solution Method)—solutions: Two aqueous samples where one sample contained 100 mM $Mg^{2+}$ ions while the other sample contained 100 mM $Ca^{2+}$ ions. Both samples had a constant background of 5 mM HEPES buffer titrated to pH=7.4 at 37C and an ionic strength of 160 mM (adjusted by addition of NaCl).

FIM (Fixed Interference Method)—solutions: Eight aqueous samples with different concentrations of $Mg^{2+}$ ions {0.01; 0.05; 0.10; 0.50; 1.00; 5.00; 10.00; 50.00}mM in a constant background of 1.25 mM $Ca^{2+}$ ions, 5 mM HEPES buffer titrated to pH=7.4 at 37C and an ionic strength of 160 mM (adjusted by addition of NaCl).

Standard solutions: Five aqueous samples spanning the physiological relevant concentration range of $Mg^{2+}$ ions from 0.2 mM to 2.5 mM in a constant background of 1.25 mM $Ca^{2+}$ ions, 5 mM HEPES buffer titrated to pH=7.4 at 37C and an ionic strength of 160 mM (adjusted by addition of NaCl).

For each $Mg^{2+}$ ion selective electrode, the concentration of $Mg^{2+}$ ions (cMg) in the sample was calculated as described in Example 2. Selectivity constants $K_{Mg,Ca}^{pot}$ and sensitivities determined from measurements on SSM- and/or the FIM-solutions were calculated directly on basis of electrode signals in accordance with the Separate Solution Method (SSM) and Fixed Interference Method (FIM) described in Umezawa et al. (2000) Pure Appl Chem 72:1851.

TABLE 5

Sensitivities (S) and selectivity constants ($K_{Mg,Ca}^{pot}$) determined by different methods for ion selective electrodes prepared with membrane IDs: "OPP", "OBA", "OBS", "DBS" and "Tetrakis".

| Parameter | Method of determination | Membrane ID | | | | |
|---|---|---|---|---|---|---|
| | | OPP | OBA | OBS | DBS | Tetrakis |
| S [mV] | FIM | 30.24 | 13.79 | 10.35 | 27.22 | 3.42 |
| | Calibration (NE) | 29.68 | 27.77 | 14.80 | 17.60 | NA |
| $K_{Mg,Ca}^{pot}$ [-] | FIM | 0.36 | NA | NA | 0.81 | NA |
| | SSM | 0.29 | 0.45 | 0.66 | 0.39 | 1.12 |
| | Calibration (NE) | 0.38 | 2.16 | 3.25 | 0.25 | NA |

TABLE 6 cMg [mM] in aqueous samples with different concentrations of $Mg^{2+}$ ions measured with ion selective electrodes prepared with membrane IDs: "OPP", "OBA", "OBS", "DBS" and "Tetrakis".

| Sample | OPP | OBA | OBS | DBS | Tetrakis |
|---|---|---|---|---|---|
| 0.200 mM $Mg^{2+}$ | 0.198 (0.007) | −1.780 (0.044) | −3.186 (0.83) | 0.414 (0.025) | NA |
| 0.598 mM $Mg^{2+}$ | 0.630 (0.003) | −1.767 (0.039) | −3.181 (0.827) | 0.816 (0.025) | NA |
| 0.991 mM $Mg^{2+}$ | 1.076 (0.007) | −1.748 (0.031) | −3.169 (0.823) | 1.268 (0.027) | NA |
| 1.744 mM $Mg^{2+}$ | 1.925 (0.017) | −1.683 (0.04) | −3.115 (0.82) | 2.292 (0.034) | NA |
| 2.497 mM $Mg^{2+}$ | 2.797 (0.027) | −1.638 (0.043) | −3.078 (0.823) | 3.527 (0.041) | NA |
| Slope | 1.133 | 0.065 | 0.050 | 1.359 | NA |
| Intercept | −0.041 | −1.802 | −3.206 | 0.024 | NA |
| R2 | 1.000 | 0.669 | 0.003 | 0.992 | NA |

Results and Conclusions

The OPP and DBS membranes obtain linear response slopes in the upper cMg-range spanned by the FIM solutions (FIG. 1). The response slopes are close to the theoretically expected Nernst sensitivity ('−'30 mV/decade) towards a divalent ion (Table 5). The other three membranes do not obtain linear response slopes within that range and hence meaningful selectivity constants based on the FIM-solutions cannot be calculated. Accordingly, these membranes are not immediately applicable for measurements within the physiological relevant cMg-range (0.2-2.5 mM) at physiological cCa and cNa background levels, since the changes in response signals towards changes in cMg are very low if not zero in that range (FIG. 1). However, the OBA and OBS membranes do have an improved Mg selectivity over both $Ca^{2+}$ and $Na^+$ ions when compared to the Tetrakis variant (see below) and thus could be used for higher Mg ranges, or with some optimization of the amounts of the components, be made more suitable for physiological ranges. Noteworthy, the Tetrakis membrane has a negative signal response on the FIM-solution with cMg=50 mM. Since the concentration of sodium ions is very low in that solution (~20 mM) compared to the other FIM-solutions (~124-155 mM) this indicates that the Tetrakis membrane is affected by a high level of interference from sodium ions.

None of the membranes containing lipophilic acids (or acid salts) show a similar behavior as the Tetrakis membrane with respect to changes in sodium ion concentration (FIG. 1). Also, when comparing the selectivity constants based on the SSM-solutions all of these membranes have a selectivity constant below 1 (Table 5), i.e., the membranes respond to $Mg^{2+}$ ions more selectively than to $Ca^{2+}$ ions. In contrast, the Tetrakis membrane has a selectivity constant above 1 (Table 5), meaning it is less selective towards $Mg^{2+}$ ions than towards $Ca^{2+}$ ions. Hence, all four membranes containing a lipophilic acid (or acid salt) have improved Mg-selectivity over both $Ca^{2+}$ and $Na^+$ ions when compared to the Tetrakis variant containing a standard lipophilic salt.

When calibrating the membranes in a complex solution background, which is suitable for a simultaneous calibration of other sensors, e.g. Na, K, Ca, Cl, pH, $PO_2$, $pCO_2$, Glucose and Lactate sensors, the best correspondence between the calibrated sensitivities and selectivity constants and those based on FIM- and SSM-solutions is obtained for the OPP membrane (Table 5). Accordingly, this membrane measures most precisely and accurately on the standard solutions covering the physiological relevant cMg-range (Table 6). No calibration values or cMg-values on standard solutions are shown for the Tetrakis membrane (Table 5 and Table 6), since it could not be calibrated in the complex solution background, i.e. no physical meaningful solution to the Nicolsky-Eisenman (NE) equation could be found, which again indicates that it also has a significant selectivity towards other ions than $Mg^{2+}$ and $Ca^{2+}$, e.g. $Na^+$ ions.

Example 4: Performance of Membranes Comprising Alternative Ionophores

Five membranes containing an Mg-selective ionophore and a single lipophilic salt were prepared in order to study the effect on membrane performance when using alternative ionophores in combination with a single lipophilic acid (or acid salt). Three ionophores: 4,7-diundecyl-1,10-phenanthroline [DUP], 4-undecyl-1,10-phenanthroline [MUP] and ETH5506, were tested in combination with $Mx(OPP)_2$ (hemi-Mx bis[4-octylphenyl]phosphate with Mx={calcium;magnesium}) as lipophilic salt. DUP and ETH5506 were also tested in combination with Tetrakis (Potassium tetrakis-(4-chlorophenyl) borate) as lipophilic salt.

The five membranes were prepared as described in Example 1, except that the compositions were as follows and that only $Mg(OPP)_2$ was pre-dissolved in the cyclohexanone before adding the remaining components. The compositions were made to ensure identical ratios between the concentrations of ionophores and lipophilic anions in the membranes. The volumes of the two membranes comprising the ETH5506 ionophore were scaled down by a factor of 6 compared to those comprising the DUP and MUP ionophores. The membranes comprising the DUP ionophore are identical to the "OPP" and "Tetrakis" membranes described in Example 3.

| Membrane ID = DUP_OPP OBS: Identical to membrane ID "OPP" in example 3 ||
|---|---|
| Compound | Quantity (g) |
| See membrane ID "OPP" in example 3 | See membrane ID "OPP" in example 3 |

| Membrane ID = DUP_Tetrakis OBS: Identical to membrane ID "Tetrakis" in example 3 ||
|---|---|
| Compound | Quantity (g) |
| See membrane ID "Tetrakis" in example 3 | See membrane ID "Tetrakis" in example 3 |

| Membrane ID = MUP_OPP ||
|---|---|
| Compound | Quantity (g) |
| Poly(vinyl chloride-co-acrylic acid (carboxylated PVC - 1.8% carboxyl basis - MW ~220,000 | 0.3360 |
| Poly(vinyl chloride-co-vinyl acetate-co-vinyl alcohol) - PVC co-polymer containing 3% of vinyl acetate and 6% of vinyl alcohol - Mr ~24,500 (Fluka 27827) | 0.6734 |
| 4-hexylphenyl 2-nitrophenyl ether (NHPE) | 2.1000 |
| Cyclohexanone | 7.2386 |
| hemi-calcium bis[4-octylphenyl]phosphate | 0.0288 |
| hemi-magnesium bis[4-octylphenyl]phosphate [MgOPP] | 0.1514 |
| 4-undecyl-1,10-phenanthroline | 0.1805 |

| Membrane ID = ETH5506_OPP ||
|---|---|
| Compound | Quantity (g) |
| Poly(vinyl chloride-co-acrylic acid (carboxylated PVC - 1.8% carboxyl basis - MW ~220,000 | 0.0560 |
| Poly(vinyl chloride-co-vinyl acetate-co-vinyl alcohol) - PVC co-polymer containing 3% of vinyl acetate and 6% of vinyl alcohol - Mr ~24,500 (Fluka 27827) | 0.1122 |
| 4-hexylphenyl 2-nitrophenyl ether (NHPE) | 0.3500 |
| Cyclohexanone | 1.2064 |
| hemi-magnesium bis[4-octylphenyl]phosphate [MgOPP] | 0.0075 |
| ETH5506 | 0.0233 |

| Membrane ID = ETH5506_Tetrakis ||
|---|---|
| Compound | Quantity (g) |
| Poly(vinyl chloride-co-acrylic acid (carboxylated PVC - 1.8% carboxyl basis - MW ~220,000 | 0.0560 |
| Poly(vinyl chloride-co-vinyl acetate-co-vinyl alcohol) - PVC co-polymer containing 3% of vinyl acetate and 6% of vinyl alcohol - Mr ~24,500 (Fluka 27827) | 0.1122 |
| 4-hexylphenyl 2-nitrophenyl ether (NHPE) | 0.3500 |
| Cyclohexanone | 1.2064 |
| Potassium tetrakis-(4-chlorophenyl) borate | 0.0076 |
| ETH5506 | 0.0233 |

Each membrane was dispensed onto four identical electrodes each positioned on identical electrode arrays, which also contained $Ca^{2+}$ ion selective electrode. The membranes were dispensed as described in Example 1. Each electrode array was placed into a measuring chamber in a test analyzer as described in Example 2.

The $Mg^{2+}$ ion selective electrodes were calibrated as described in Example 3. The $Ca^{2+}$ ion selective electrodes were also calibrated. The calibrated sensors were then subjected to measurements on SSM-solutions, FIM-solutions and Standard solutions as described in Example 3.

For each $Mg^{2+}$ ion selective electrode, the concentration of $Mg^{2+}$ ions (cMg) in the sample was calculated as described in Example 2. Selectivity constants $K_{Mg,Ca}^{pot}$ and sensitivities determined from measurements on SSM- and/or the FIM-solutions were calculated as described in Example 3.

TABLE 7

Sensitivities (S) and selectivity constants ($K_{Mg,Ca}^{pot}$) determined by different methods for ion selective electrodes prepared with membrane IDs: "DUP_OPP", "DUP_Tetrakis", "MUP_OPP", "ETH5506_OPP" and "ETH5506_Tetrakis".

| Parameter | Method of determination | DUP_OPP | DUP_Tetrakis | MUP_OPP | ETH5506_OPP | ETH5506_Tetrakis |
|---|---|---|---|---|---|---|
| S [mV] | FIM | 30.24 | 3.42 | 30.16 | 1.38 | 0.65 |
|  | Calibration (NE) | 29.68 | NA | 29.09 | 3.46 | NA |
| $K_{Mg,Ca}^{pot}$ [-] | FIM | 0.36 | NA | 0.27 | NA | NA |
|  | SSM | 0.29 | 1.12 | 0.20 | 5.63 | 2.41 |
|  | Calibration (NE) | 0.38 | NA | 0.25 | 2.79 | NA |

TABLE 8 cMg [mM] in aqueous samples with different concentrations of $Mg^{2+}$ ions measured with ion selective electrodes prepared with membrane IDs: "DUP_OPP", "DUP_Tetrakis", "MUP_OPP", "ETH5506_OPP" and "ETH5506_Tetrakis".

| Sample | DUP_OPP | DUP_Tetrakis | MUP_OPP | ETH5506_OPP | ETH5506_Tetrakis |
|---|---|---|---|---|---|
| 0.200 mM $Mg^{2+}$ | 0.198 (0.007) | NA | 0.207 (0,005) | 2.89 (0.810) | NA |
| 0.598 mM $Mg^{2+}$ | 0.630 (0.003) | NA | 0.63 (0,002) | 3.92 (0.801) | NA |
| 0.991 mM $Mg^{2+}$ | 1.076 (0.007) | NA | 1.069 (0,003) | 4.386 (0.979) | NA |
| 1.744 mM $Mg^{2+}$ | 1.925 (0.017) | NA | 1.907 (0,005) | 5.374 (0.930) | NA |
| 2.497 mM $Mg^{2+}$ | 2.797 (0.027) | NA | 2.765 (0,013) | 6.829 (1.278) | NA |
| Slope | 1.133 | NA | 1.115 | 1.617 | NA |
| Intercept | −0.041 | NA | −0.030 | 2.729 | NA |
| R2 | 1.000 | NA | 1.000 | 0.668 | NA |

Results and Conclusions

Figure 2:
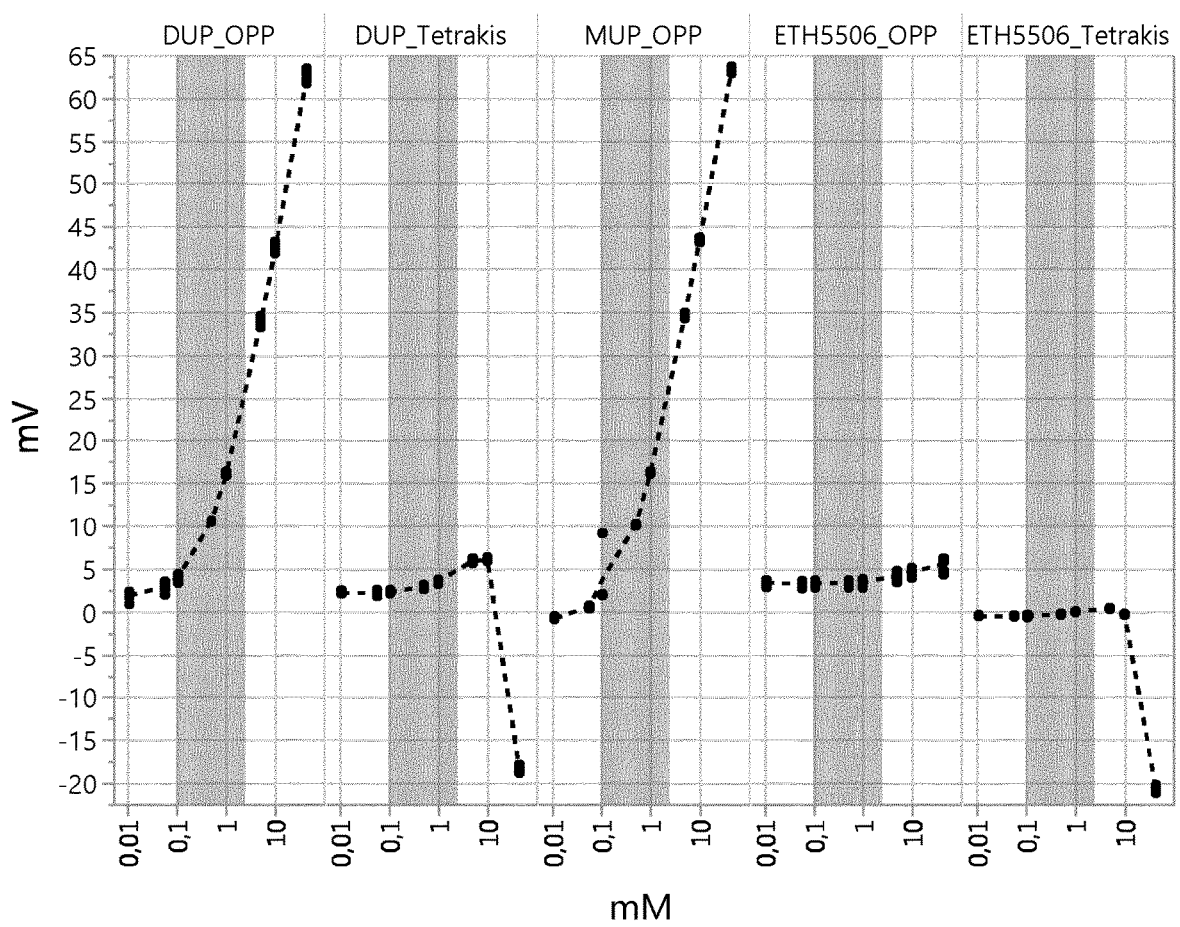
FIG. 2. Signals in mV as function of true cMg values as recorded for the FIM-solutions used to determine the selectivity constants ($KMgc_a$) and sensitivities (S) of ion selective electrodes prepared with membrane IDs: "DUP_OPP", "DUP_Tetrakis", "MUP_OPP", "ETH5506_OPP" and "ETH5506_Tetrakis". Gray shaded areas indicate the physiological relevant measurement range (0.1-2.5 mM) for ionized magnesium. The x-axis is logarithmic.

The DUP_OPP and MUP_OPP membranes obtain linear response slopes in the upper cMg-range spanned by the FIM solutions (FIG. 2). The response slopes are close to the theoretically expected Nernst sensitivity (~30 mV/decade) towards a divalent ion (Table 7). The other three membranes do not obtain linear response slopes within that range and hence meaningful selectivity constants based on the FIM-solutions cannot be calculated. Accordingly, these membranes are not immediately applicable for measurements within the physiological relevant cMg-range (0.2-2.5 mM) at physiological cCa and cNa background levels, since the changes in response signals towards changes in cMg are very low if not zero in that range (FIG. 2). However, the ETH5506_OPP membrane shows less interference from sodium ions when compared to the Tetrakis variant (see below) and thus could be used for higher Mg ranges, or with some optimization of the amounts of the components, be made more suitable for physiological ranges. Noteworthy, both membranes containing the tetrakis salt (DUP_Tetrakis and ETH5506_Tetrakis) have a negative signal response on the FIM-solution with cMg=50 mM. Since the concentration of sodium ions is very low in that solution (~20 mM) compared to the other FIM-solutions (~124-155 mM) this indicates that the membranes containing tetrakis are affected by a high level of interference from sodium ions.

None of the membranes containing the lipophilic acid salt $(Mx(OPP)_2)$ show a similar behavior as the Tetrakis membrane with respect to changes in sodium ion concentration (FIG. 2). When comparing the selectivity constants based on the SSM-solutions all of these membranes, except ETH5506_OPP, have a selectivity constant below 1 (Table 7), i.e., the membranes respond to $Mg^{2+}$ ions more selectively than to $Ca^{2+}$ ions. In contrast, both membranes containing the tetrakis salt (DUP_Tetrakis and ETH5506_Tetrakis) and the ETH5506_OPP have a selectivity constant above 1 (Table 7), meaning they are less selective towards $Mg^{2+}$ ions than towards $Ca^{2+}$ ions. Hence, all membranes containing a lipophilic acid salt $(Mx(OPP)_2)$ have improved Mg-selectivity over $Na^+$ ions when compared to those containing the standard lipophilic tetrakis salt. Further, the combination of a lipophilic acid salt and a phenanthroline based ionophore (DUP_OPP and MUP_OPP) improves the Mg-selectivity over $Ca^{2+}$ ions when compared to the ETH5506_OPP membrane, which contains a non-phenanthroline based ionophore.

When calibrating the membranes in a complex solution background, which is suitable for a simultaneous calibration of other sensors, e.g. Na, K, Ca, Cl, pH, $PO_2$, $pCO_2$, Glucose and Lactate sensors, the best correspondence between the calibrated sensitivities and selectivity constants and those based on FIM- and SSM-solutions is obtained for the DUP_OPP and MUP_OPP membranes (Table 7). Accordingly, these membrane measures most precisely and accurately on the standard solutions covering the physiological relevant cMg-range (Table 8). No calibration values or cMg-values on standard solutions are shown for the membranes containing the tetrakis salt (Table 7 and Table 8), since they could not be calibrated in the complex solution background, i.e. no physical meaningful solutions to the Nicolsky-Eisenman (NE) equation could be found, which again indicates that they also have a significant selectivity towards other ions than $Mg^{2+}$ and $Ca^{2+}$, e.g. $Na^+$ ions.

The invention claimed is:

1. A magnesium ion selective membrane comprising:
   a. an ionophore that is not charged; and
   b. a lipophilic compound comprising an acidic group, wherein the lipophilic compound is a compound of the formula I:

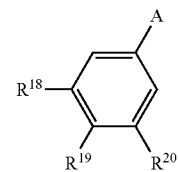

wherein A comprises an acidic group,
   wherein one, two or all three of $R^{18}$, $R^{19}$ and $R^{20}$ is a $C_{4-18}$ group, which is a $C_{4-18}$ alkyl group, a $C_{4-18}$ alkenyl group, a $C_{4-18}$ alkynyl group, or an amide-containing $C_{4-18}$ group, wherein said $C_{4-18}$ group is linear at positions 1, 2 and 3, counting from the phenyl group, or in total only has one side chain at said positions 1, 2 and 3,
   and wherein any remaining of $R^{18}$, $R^{19}$ and $R^{20}$ independently are hydrogen, or a linear $C_{1-18}$ alkyl,
   or a salt of said lipophilic compound.

2. The membrane according to claim 1, wherein the ionophore is a phenanthroline compound which is 1,10-phenanthroline or a substituted form thereof.

3. The membrane according to claim 2, wherein the phenanthroline compound is a compound of the formula II:

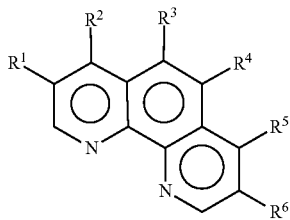

wherein each of $R^1$-$R^6$ is any of:
H;
any of F, Cl, Br, I, $NO_2$, CN, or $CF_3$;
$C_{1-18}$ alkyl;
$C_{1-18}$ aryl;
$C_{1-18}$ alkenyl;
$(CH_2)_m Y$, wherein m is 0 or an integer from 1 to 4, Y is any of —$OR^7$, —$NR^7R^8$, —$OCOR^7$, —$NR^7COR^8$, —$COR^7$, —$COOR^7$, $SO_3R^7$, —$OSiR^7R^8R^9$, —$PO_4R^7R^8$, —$PO_3R^7R^8$, wherein each of $R^7$, $R^8$, and $R^9$ are any of H, alkyl, branched alkyl, aryl, or substituted aryl; or
$C_n$—$R^{10}R^{11}$, wherein n is 0 or an integer between 1 and 17 inclusive, $R^{10}$ is C, N, NCO, or $CH_2$—Z—$CH_2$ wherein Z is any of O, NH, S, OCO, or CO, $R^{11}$ is

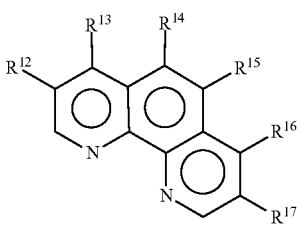

and $R^{11}$ is linked to $R^{10}$ at any of positions 3, 4, 5, 6, 7, or 8 of $R^{11}$, $R^{12}$-$R^{17}$ are any of H, $C_{1-18}$ alkyl, $C_{1-18}$ aryl, or deleted, provided that if $R^{11}$ is linked to $R^{10}$ at position 3 of $R^{18}$ then $R^{12}$ is deleted, if $R^{18}$ is linked to $R^{10}$ at position 4 of $R^{11}$ then $R^{13}$ is deleted, if $R^{18}$ is linked to $R^{10}$ at position 5 of $R^{18}$ then $R^{14}$ is deleted, if $R^{18}$ is linked to $R^{10}$ at position 6 of $R^{18}$ then $R^{15}$ is deleted, if $R^{11}$ is linked to $R^{10}$ at position 7 of $R^{18}$ then $R^{16}$ is deleted, if $R^{18}$ is linked to $R^{10}$ at position 8 of $R^{11}$ then $R^{17}$ is deleted,
provided that one of $R^1$-$R^6$ is other than H and that each of the C atoms at positions 2 and 9 of the 1,10-phenanthroline is bonded, by the bond which does not participate in the fused ring structure, to an H.

4. The membrane according to claim 3, wherein $R^1$ to $R^6$ include a total of at least 6 carbon atoms.

5. The membrane according to claim 3, wherein one or more of $R^1$, $R^2$, $R^3$, $R^4$, $R^5$ and $R^6$ is an alkyl group having between 1 and 18 carbon atoms.

6. The membrane according to claim 3, wherein the phenanthroline compound is 4-undecyl-1,10-phenanthroline or 4,7-diundecyl-1,10-phenanthroline.

7. The membrane according to claim 1, wherein the acidic group comprised within group A of formula I is selected from the group consisting of: a carboxylic acid, a sulfonic acid, a sulfuric acid monoester, a sulfonamide, a phosphonic acid, a phosphoric acid, an arsenic acid, a sulfinic acid, and a thiocarboxylic acid.

8. The membrane according to claim 7, wherein the lipophilic compound is a compound of the formula:

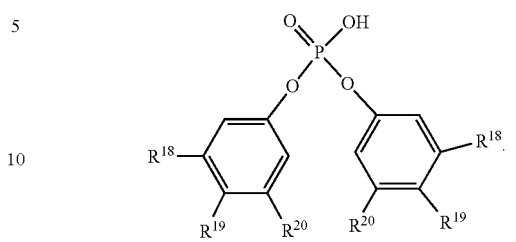

9. The membrane according to claim 1, wherein only one of $R^{18}$, $R^{19}$ or $R^{20}$ is a $C_{4-18}$ alkyl group and the others are hydrogen.

10. The membrane according to claim 1, wherein $R^{19}$ is a $C_{4-18}$ alkyl group as defined in claim 1 and $R^{18}$ and $R^{20}$ are hydrogen.

11. The membrane according to claim 1, wherein said $C_{4-18}$ alkyl group(s) comprise(s) at least 6 carbon atoms.

12. The membrane according to claim 1, wherein the lipophilic compound is a lipophilic salt and said lipophilic salt is hemi-calcium bis[4-octylphenyl]phosphate, hemi-magnesium bis[4-octylphenyl]phosphate or a mixture thereof.

13. The membrane according to claim 12, wherein the lipophilic salt is a mixture containing at least 50% hemi-magnesium bis[4-octylphenyl]phosphate.

14. The membrane according to claim 1, wherein the molar ratio between the ionophore and the lipophilic compound or the anion of the lipophilic salt is between 2:1 and 1:1.

15. A process for preparing a magnesium ion selective membrane comprising mixing the components specified in claim 1 in a solvent, dispensing the resulting solution on a desired support and allowing the solvent to evaporate.

16. An electrode for determining the magnesium ion concentration of a liquid sample comprising the membrane of claim 1.

17. A potentiometric sensor for determining the magnesium ion concentration of a liquid sample comprising the electrode of claim 16 and a reference electrode.

18. A method for determining the magnesium ion concentration of a liquid sample comprising contacting said sample with a potentiometric senor according to claim 17 and determining the magnesium ion concentration based on signal provided by said potentiometric sensor.

19. A method for diagnosing a disease or disorder, said method comprising performing the method according to claim 18 on a sample of a subject, said method further comprising comparing the magnesium ion concentration in said sample with a reference magnesium ion concentration, to diagnose hypomagnesemia or hypermagnesemia in said subject.

20. A method for determining the magnesium ion concentration of a liquid sample comprising contacting said sample with an electrode according to claim 16 and determining the magnesium ion concentration based on signal provided by said electrode.

21. A method for diagnosing a disease or disorder, said method comprising performing the method according to claim 20 on a sample of a subject, said method further comprising comparing the magnesium ion concentration in said sample with a reference magnesium ion concentration to diagnose hypomagnesemia or hypermagnesemia in said subject.

22. A magnesium ion selective membrane comprising:
i) an ionophore covalently linked to an acidic group via a spacer wherein said spacer comprises at least one carbon atom; or
ii) a salt of said ionophore covalently linked to an acidic group,
wherein the ionophore is not charged.

* * * * *